(12) United States Patent
Dumesic et al.

(10) Patent No.: US 7,572,925 B2
(45) Date of Patent: Aug. 11, 2009

(54) CATALYTIC PROCESS FOR PRODUCING FURAN DERIVATIVES IN A BIPHASIC REACTOR

(75) Inventors: James A. Dumesic, Madison, WI (US); Yuriy Román-Leshkov, Madison, WI (US); Juben N. Chheda, Houston, TX (US)

(73) Assignee: Wisconsin Alumni Research Foundation, Madison, WI (US)

( * ) Notice: Subject to any disclaimer, the term of this patent is extended or adjusted under 35 U.S.C. 154(b) by 16 days.

(21) Appl. No.: 11/757,461

(22) Filed: Jun. 4, 2007

(65) Prior Publication Data
US 2008/0033188 A1 Feb. 7, 2008

Related U.S. Application Data

(60) Provisional application No. 60/811,343, filed on Jun. 6, 2006.

(51) Int. Cl.
*C07D 307/46* (2006.01)
*C07D 307/50* (2006.01)
(52) U.S. Cl. ........................ 549/488; 549/489
(58) Field of Classification Search .................. 549/488, 549/489
See application file for complete search history.

(56) References Cited

U.S. PATENT DOCUMENTS

| | | | |
|---|---|---|---|
| 2,750,394 A | 6/1956 | Peniston | |
| 2,917,520 A | 12/1959 | Cope | |
| 2,929,823 A | 3/1960 | Garber et al. | |
| 2,994,645 A | 8/1961 | Jones et al. | |
| 3,118,912 A | 1/1964 | Smith | |
| 3,201,331 A | 8/1965 | Hunter | |
| 4,154,744 A * | 5/1979 | Hamada et al. | 549/483 |
| 4,339,387 A | 7/1982 | Fléche et al. | |
| 4,549,031 A | 10/1985 | Chen et al. | |
| 4,740,605 A | 4/1988 | Rapp | |
| 4,971,657 A | 11/1990 | Avignon et al. | |
| 6,603,026 B2 | 8/2003 | Lightner | |
| 2003/0032819 A1 | 2/2003 | Lightner | |

FOREIGN PATENT DOCUMENTS

| | | |
|---|---|---|
| EP | 0 082 689 | 6/1983 |
| FR | 2663933 | 1/1992 |
| FR | 2664273 | 1/1992 |
| FR | 2669635 | 5/1992 |
| GB | 591858 | 5/1944 |
| GB | 600871 | 4/1948 |
| GB | 876463 | 2/1962 |
| GB | 2 131 014 A | 6/1984 |
| WO | WO 9210486 | 6/1992 |
| WO | WO 2005018799 | 3/2005 |

OTHER PUBLICATIONS

Roman-Leshkov et al., "Phase Modifiers Promote Efficient Production of Hydroxymethylfurfural from Fructose," *Science*, vol. 312, No. 5782 (2006), 1993-1997.
Huber et al., "Production of Liquid Alkanes by Aqueous-Phase Processing of Biomass-Derived Carbohydrates," *Science*, vol. 308, No. 5727 (2005), 1446-1450.
Antal, M.J.J. et al., Mechanism of formation of 5-(hydroxymethyl(-2-furaldehyde from D-fructose and sucrose, *Carbohydrate Research* 199, 91 (1990).
Benvenuti, F. et al., Heterogeneous zirconium and titanium catalysts for the selective synthesis of 5-hydroxymethyl-2-furaldehyde from carbohydrates, *Applied Catalysis A: General* 193, 147 (2000).
Bicker, M. et al., Dehydration of fructose to 5-hydroxymethylfurfural in sub- and supercritical acetone, *Green Chemistry* 5, 280 (2003).
Carlini, C. et al., Selective saccharides dehydration to 5-hydroxymethyl-2-furaldehyde by heterogenous niobium catalysts *Applied Catalysis A: General* 183, 295 (1999).
Carlini, C. et al., Heterogeous catalysts based on vanadyl phosphate for fructose dehydration to 5-hydroxymethyl-2-furaldehyde, *Applied Catalysis A: General* 275, 111 (2004).
El Hajj, T. et al., Synthèse de l'hydroxyméthyl-5 furanne carboxaldéhyde-2 et de ses dérivés par traitement acide de sucres sur résines échangeuses d'ions, *Bulletin de la Societe Chimique de France* 5, 855 (1987).
Gaset, A. et al., procédés d'obtention de l'hydroxyméthyl-5 furannecarboxyaldéhyde-2, *Informations Chimie* 212, 179 (1981).
Huber, G.W. et al., Production of Liquid Alkanes by Aqueous-Phase Processing of Biomass-DErived Carbohydrates, *Science* 308, 1446 (2005).
Nakamura, Y. et al., The Dehydratioin of D-Fructose to 5-Hydroxymethyl-2-furaldehyde, *Bulletin of the Chemical Society of Japan* 53, 3705 (1980).
Rigal, L. et al., Selective Conversion of D-Fructose to 5-Hydroxymethyl-2-furancarboxadehyde Using a Water-Solvent-Ion-Exchange Resin Triphasic System, *Industrial Engineering and Chemical Product Research Development* 20, 719 (1981).
Rivalier, P. et al., Development of a continuous catalytic heterogeneous column reactor with simultaneous extraction of an intermediate product by an organic solvent circulating in countercurrent manner with the aqueous phase, *Catalysis Today* 24, 165 (1995).
Seri, K. et al., Catalytic Activitiy of Lanthanide(III) Ions for the Dehydration of Hexose to 5-Hydroxymethyl-2-furaldehyde in Water, *Bulletin of the Chemical Society of Japan* 74, 1145 (2001).

(Continued)

*Primary Examiner*—Bernard Dentz
(74) *Attorney, Agent, or Firm*—Joseph T. Leone, Esq.; DeWitt Ross & Stevens S.C.

(57) ABSTRACT

Described is a catalytic process for converting sugars to furan derivatives (e.g. 5-hydroxymethylfurfural, furfural, dimethylfuran, etc.) using a biphasic reactor containing a reactive aqueous phase and an organic extracting phase. The process provides a cost-effective route for producing di-substituted furan derivatives. The furan derivatives are useful as value-added intermediates to produce polymers, as precursors to diesel fuel, and as fuel additives.

27 Claims, 11 Drawing Sheets

OTHER PUBLICATIONS

Chheda, et al., "An overview of dehydration, aldol condensation and hydrogenation processes for production of liquid alkanes from biomass-derived carbohydrates," *Catalysis Today*, 2007, vol. 123, pp. 59-70.

Brown, D.W. et al., Dehydration Reactions of Fructose in Non-aqueous Media, *Journal of Chemical Technology and Biotechnology* 32, 920 (1982).

Cottier, L. et al., 5-Hydroxymethylfurfural syntheses and chemical transformations, *Trends Heterocycl. Chem.*, vol. 2, 233-248 (1991).

Dadgar et al., The Production of Hydroxymethyl Furfural from Sawdust, *Biotechnology and Bioengineering Symp.*, No. 13, 41-52 (1983).

Dias, A.S. et al., Dehydration of xylose into furfural over micro-mesoporous sulfonic acid catalysts, *Journal of Catalysis* 229, 414 (2005).

Harris, J.F. et al., Preparation and Properties of Hydroxymethylfurfural, *Forest Products Journal* 10, 125 (1960).

Kuster, B.M.F., 5-Hydroxymethylfurfural (HMF). A Review Focusing on its Manufacture, *Starch* 42, 314 (1990).

Lewkowski, J., Synthesis, Chemistry and Applications of 5-Hydroxymethyl-furfural And Its Derivatices, *Arkivoc* Available electronically at www.arkat-usa.org/ark/journal/2001/I01_General/403/0113.pdf 17 (2001).

Mercadier, D. et al., Synthesis of 5-Hydroxymethyl-2-furancarboxyaldehyde Catalysed by Cationic Exchange Resins. Part 1. Choice of the Catalyst and the Characteristics of the Reaction Medium, *J. Chem. Tech. Biotechnol.* 31:489-496 (1981).

Moreau, C. et al., Recent catalytic advances in the chemistry of substituted furans from carbohydrates and in the ensuing polymers, *Topics in Catalysis* 27, 11 (2004).

Moye, C.J., 5-Hydroxymethylfurfural, *Rev. Pure and Appl. Chem.*, 14:161-170 (1964).

Musau, R. et al., The Preparation of 5-Hydroxymethyl-2-Furaldehyde (HMF) from D-Fructose in the Presence of DMSO, *Biomass* 13:67-74 (1987).

Szmant, H.H. et al., The Preparation of 5-Hydroxymethylfurfuraldehyde from High Fructose Corn Syrup and Other Carbohydrates, *Journal of Chemical Technology and Biotechnology* 31, 135 (1981).

Van Dam, H.E. et al., The Conversion of Fructose and Glucose in Acidic Media: Formation of Hydroxymethylfurfural, *Starch* 38, 95 (1986).

Werpy, T. et al., *Top Value Added Chemicals From Biomass* Available electronically at http://www.osti.gov/bridge (2004).

* cited by examiner

CATALYTIC PROCESS FOR PRODUCING FURAN DERIVATIVES IN A BIPHASIC REACTOR

CROSS-REFERENCE TO RELATED APPLICATIONS

Priority is hereby claimed to provisional application Ser. No. 60/811,343, filed Jun. 6, 2006, which is incorporated herein by reference.

FEDERAL FUNDING STATEMENT

This invention was made with United States government support awarded by the following agencies: USDA/CSREES 2003-35504-13752 and NSF 0456693. The United States has certain rights in this invention.

FIELD OF THE INVENTION

The invention is directed to a process for selectively dehydrating carbohydrates, (preferably sugars, e.g., fructose, glucose, xylose) to yield furan derivatives such as 5-hydroxymethylfurfural (HMF) and furfural. Particularly advantageous is that the process operates at high sugar concentrations in the reactant feed (preferably from about 10 to about 50 wt %), achieves high yields (>80% HMF selectivity at 90% sugar conversion when using fructose as the reactant), and delivers the furan derivative in a separation-friendly solvent. The process uses a two-phase reactor system wherein the sugar is dehydrated in an aqueous phase (preferably using an acid catalyst such as HCl or an acidic ion-exchange resin). The furan derivative product is continuously extracted into an organic phase (preferably 1-butanol) thus reducing side reactions.

BACKGROUND

Since at least as early as the mid-1960's, scientific and economic forecasters have been predicting an approaching era of diminishing availability of petrochemical resources to produce the energy and chemical materials needed by industrialized societies. On one hand, discoveries of new petroleum reserves and new petroleum production technologies (e.g., deep-water, off-shore drilling) have staved off an economically catastrophic shortage of crude oil. On the other hand, rapidly industrializing national economies (most notably China and India), coupled with political instability in petroleum-producing regions (most notably the middle east, Nigeria, and Venezuela), have pushed oil prices to record levels. In early 2006, the price of a barrel of crude oil topped $70 for the first time in history. Environmental, ecological, and political considerations have also effectively made certain proven reserves of petroleum off-limits to commercial exploitation. For example, production of petroleum from proven reserves in the Artic National Wildlife Refuge in Alaska has been (and for the foreseeable future, will continue to be) blocked by federal and state legislation to preserve this unique natural landscape from human encroachment.

The rippling effect of high crude oil prices on national economies is profound. Not only are gasoline and diesel the principal transportation fuels worldwide, crude petroleum also yields a vast array of chemicals that are feedstocks for an equally vast array of products, from plastics to pesticides. Thus, high crude oil prices spur worldwide inflation as producers pass on their increased costs of production to consumers.

The economic difficulties caused by increasing demand coupled with diminishing supply is driving efforts to develop alternative and sustainable ways to meet energy and raw material needs. The *Roadmap for Biomass Technologies in the United States* (U.S. Department of Energy, Accession No. ADA436527, December 2002), authored by 26 leading experts, has predicted a gradual shift from a petroleum-based economy to a more carbohydrate dependent economy. This official document predicts that by 2030, 20% of transportation fuel and 25% of chemicals consumed in the United States will be produced from biomass. Such a shift away from petroleum-based technologies requires developing innovative, low-cost separation and depolymerization processing technologies to break down the highly oxygen-functionalized, polysaccharide molecules found in raw biomass, to yield useful bio-derived materials and fuels. In short, abundant biomass resources can provide alternative routes for a sustainable supply of both transportation fuels and valuable intermediates (e.g., alcohols, aldehydes, ketones, carboxylic acid, esters) for production of drugs and polymeric materials. However, unless these alternative routes can be implemented at a production cost roughly comparable to the corresponding production cost when using petroleum feedstocks, the transition will inevitably be accompanied by severe economic dislocations. It is not enough that the transition can be accomplished; to avoid economic upheaval, the transition must be accomplished in an economically feasible fashion.

Furan derivatives (such as furfural (Fur) and 5-hydroxymethylfurfural (HMF)) derived from renewable biomass resources have potential as substitutes for petroleum-based building blocks used to produce plastics and fine chemicals. For example, HMF can be converted to 2,5-furandicarboxylic acid (FDCA) by selective oxidation; FDCA can be used as a replacement for terephthalic acid in the production of polyesters such as polyethyleneterephthalate (PET) and polybutyleneterephthalate (PBT). Reducing HMF leads to products such as 2,5-dihydroxymethylfuran and 2,5-bis(hydroxymethyl)tetrahydrofuran, which can function as the alcohol components in the production of polyesters (thereby leading to completely biomass-derived polymers when combined with FDCA). Additionally, disubstituted furan derivates obtained from HMF serve as an important component of pharmacologically active compounds associated with a wide spectrum of biological activities. Furfural is also a key chemical for the commercial production of furan (via catalytic decarbonylation) and tetrahydrofuran (via hydrogenation), thereby providing a biomass-based alternative to the corresponding petrochemical production route (via dehydration of 1,4-butanediol).

Furfural is primarily used in refining lubricating oil. Furfural is also used in condensation reactions with formaldehyde, phenol, acetone or urea to yield resins with excellent thermosetting properties and extreme physical strength. Methyl-tetrahydrofuran (MeTHF), a hydrogenated form of furfural, is a principal component in P-series fuel, which is developed primarily from renewable resources. ("P-series fuel" is an official designation promulgated by the U.S. Dept. of Energy for a fuel blend comprised of pentanes, ethanol, and biomass-derived MeTHF. See 10 CFR §490.)

However, as indicated by various authors, the industrial use of HMF as a chemical intermediate is currently impeded by high production costs. Perhaps because of the high cost of production, a number of U.S. and foreign patents describe methods to produce HMF. See, for example, U.S. Pat. Nos. 2,750,394 (to Peniston); 2,917,520 (to Cope); 2,929,823 (to Garber); 3,118,912 (to Smith); 4,339,387 (to Fleche et al.); 4,590,283 (to Gaset et al.); and 4,740,605 (to Rapp). In the foreign patent literature, see GB 591,858; GB 600,871; and GB 876,463, all of which were published in English. See also FR 2,663,933; FR 2,664,273; FR 2,669,635; and CA 2,097,812, all of which were published in French.

Producing furfural from biomass requires raw materials rich in pentosan, such as corncobs, oat hulls, bagasse, and certain woods (like beech). Even today, most furfural production plants employ batch processing using the original, acid-catalyzed Quaker Oats technology (first implemented in 1921 by Quaker Oats in Cedar Rapids, Iowa as a means to realize value from the tons of oat hulls remaining after making rolled oats). (For an exhaustive history on the production of furfural, see K. J. Zeitsch, "The Chemistry and Technology of Furfural and its Many By-Products," Elsevier, Sugar Series, No. 13, © 2000, Elsevier Science B. V.) This batch processing results in yields less than 50%, and also requires a large amount of high-pressure steam. The process also generates a significant amount of effluent.

Various researchers have tried dehydration of xylose into furfural using acid catalysts such as mineral acids, zeolites, acid-functionalized Mobile crystalline materials (MCM's) and heteropolyacids. Moreau et. al. has conducted the reaction in a batch mode using H-form faujasites and a H-mordenite catalyst, at 170° C., in a solvent mixture of water and methylisobutylketone (MIBK) or toluene (1:3 by vol) with selectivities ranging from 70-96% (in toluene) and 50-60% (in MIBK) but at low conversions. Dias et al. showed that a sulfonic acid-modified MCM-41-type catalyst displayed fairly high selectivity to furfural (~82%) at high xylose conversion (>90%) with toluene as the extracting solvent for the reactions carried out 140° C. In the patent literature, see, for example, U.S. Pat. Nos. 4,533,743 (to Medeiros et al.); 4,912,237 (to Zeitsch); 4,971,657 (to Avignon et al.), and 6,743,928 (to Zeitsch).

Abundant biomass resources are a promising sustainable supply of valuable intermediates (e.g., alcohols, aldehydes, ketones, carboxylic acids) to the chemical industry for producing drugs and polymeric materials. In this context, the high content of oxygenated functional groups in carbohydrates, the dominant compounds in biomass, is an advantage. (Which is in contrast to the drawbacks of such functionality for the conversion of carbohydrates to fuels.) However, there remains a long-felt and unmet need for efficient processes to selectively remove excess functional groups and to modify other functional groups to create commercially desirable products from biomass.

SUMMARY OF THE INVENTION

The present invention is a method for the selective dehydration of carbohydrates (preferably fructose) to produce furan derivatives (preferably 5-hydroxymethylfurfural (HMF). The method is highly useful because it provides a cost-effective route for making these valuable chemical intermediates. Indeed, HMF and its ensuing 2,5-disubstituted furan derivatives could replace key petroleum-based building blocks (1). For example, HMF can be converted to 2,5-furandicarboxylic acid (FDCA) by selective oxidation, and Werpy and Petersen (2) and Pentz (3) have suggested that FDCA can be used as a replacement for terephthalic acid in the production of polyesters such as polyethyleneterephthalate (PET) (2) and polybutyleneterephthalate (PBT). They have also suggested that the reduction of HMF can lead to products such as 2,5-dihydroxymethylfuran and 2,5-bis(hydroxymethyl)tetrahydrofuran, which can serve as alcohol components in the production of polyesters, thereby leading to completely biomass-derived polymers when combined with FDCA. In addition, HMF can serve as a precursor in the synthesis of liquid alkanes to be used, for example, in diesel fuel (4).

Unfortunately, as noted by various authors (5-8), the industrial use of HMF as a chemical intermediate is currently impeded by high production costs. Early work showed that HMF could be produced in high concentrations using high-boiling organic solvents, such as dimethylsulfoxide (DMSO), dimethylformamide, and mixtures of polyethyleneglycol (PEG) with water, over various catalysts including sulfuric acid and sulfonic acid resins; however, this approach necessitates difficult and energy intensive isolation procedures (6, 9-13). In pure water, fructose dehydration is generally nonselective, leading to many byproducts besides HMF (14). Recent advances have shown improved results in pure water or in water-miscible solvent systems (e.g., acetonitrile or acetone), but only using low initial fructose concentrations which inevitably generate low HMF concentrations (1, 10, 15, 16). Biphasic systems, where a water-immiscible organic solvent is added to extract continuously the HMF from the aqueous phase, have also been investigated using mineral acid or zeolite catalysts at temperatures above 450 K (6, 17-21). However, poor HMF partitioning into the organic streams employed in these studies necessitated large amounts of solvent, thereby requiring large energy expenditures to purify the diluted HMF product (22).

Thus, the present invention is directed to a process to make furan derivative compounds. The process comprises dehydrating a carbohydrate feedstock solution, optionally in the presence of an acid catalyst, in a reaction vessel containing a biphasic reaction medium comprising an aqueous reaction solution and a substantially immiscible organic extraction solution. The aqueous reaction solution, the organic extraction solution, or both the aqueous reaction solution and the organic extraction solution, contain at least one modifier to improve selectivity of the process to yield furan derivative compounds in general, and HMF in particular.

In the preferred embodiment, the process includes an aqueous reaction solution containing the carbohydrate, an acid catalyst, and a chemical modifier. The modifier is comprised of an inorganic salt and/or a dipolar, aprotic additive. The acid catalyst preferably is selected from the group consisting of mineral acids. The aqueous phase modifier preferably comprises an inorganic salt selected from the group consisting of metal halides, sulfates, sulfides, phosphates, nitrates, acetates, and carbonates; and the dipolar, aprotic additive is selected from the group of additives such as dimethylsulfoxide (DMSO), dimethylformamide, N-methylpyrrolidinone (NMP), acetonitrile, butyrolactone, dioxane, pyrrolidinone; water-miscible alcohols or ketones (methanol, ethanol, acetone); and water-soluble polymers such as polyethylene glycol (PEG) and poly(1-vinyl-2-pyrrolidinone) (PVP).

In the preferred versions of the invention, the organic extraction solution comprises an alcohol (1-butanol is preferred), a ketone (MIBK is preferred), and/or a chlorinated alkane (DCM is preferred) which is immiscible with the chemically modified aqueous phase. Where DCM is used, it is also preferred that the reaction be carried out without an acid catalyst. The organic extraction solution is preferably modified with a $C_1$- to $C_{12}$-alcohol, more preferably a primary or secondary, linear, branched, or cyclic $C_3$- to $C_8$-alkanol, and most preferably 2-butanol. The organic extraction solution and the aqueous reaction solution preferably are present in a volume ratio of from about 0.1:1 to about 100:1 (organic extraction solution:aqueous reaction solution). As a general rule, the dehydration reaction is carried out at a temperature ranging from about 70° C. to about 250° C. Higher temperatures may be used where the acid catalyst is heterogeneous, such as a zeolite catalyst.

The dehydration reaction is preferably carried out at pressures ranging from about 1 bar to about 200 bars, using carbohydrate feedstock solutions comprising 1-70 wt % carbohydrate (about 10 to 50 wt % is preferred).

The invention is more particularly directed to a method of making a compound of Formula I:

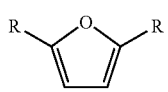

(I)

wherein each R is independently selected from the group consisting of hydrogen, $C_1$-$C_6$-alkyl, hydroxy-$C_1$-$C_6$-alkyl, acyl-$C_1$-$C_6$-alkyl, $C_1$-$C_6$-alkylcarbonyl-$C_1$-$C_6$-alkyl, and carboxy-$C_1$-$C_6$-alkyl, and provided the both R's are not simultaneously hydrogen. The method comprises dehydrating a feedstock solution comprising a carbohydrate, in the presence of an acid catalyst, in a reaction vessel containing a biphasic reaction medium. The biphasic reaction medium preferably comprises (i) an aqueous reaction solution comprising water and one or more modifiers (e.g., NaCl or DMSO); and (ii) an organic extraction solution that is immiscible with the aqueous reaction solution. Preferably, the organic extraction solution comprises, by way of non-limiting examples, 1-butanol, DCM or a mixture of MIBK and 2-butanol.

In the preferred versions of the process, the organic extraction solution comprises a solvent selected from the group consisting of unsubstituted aliphatic and aromatic hydrocarbons and halo-substituted aliphatic and aromatic hydrocarbons. Water-immiscible, linear, branched, or cyclic alcohols, ethers, and ketones may also be used as the organic extraction solution. Any combination of these solvents may also be used.

In one particularly preferred version of the invention, the aqueous reaction solution further comprises at least one salt, thereby yielding a saline aqueous reaction solution. Any salt that is non-reactive with the dehydration reaction taking place can be used. The salts comprise a cation and an anion. A non-limiting list of suitable anions that can be used in the salt in include acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, and bis-trifluorsulfonimide. A non-limiting list of suitable cations includes Group I and II metals, the most preferred of these being Na, K, Mg, and Ca. NaCl is the preferred salt. Two or more different salts my also be used. The salt can be added in small amount or added until the aqueous reaction solution is saturated in the chosen salt. When the aqueous solution contains salt, the organic extraction solution comprises a solvent that is substantially immiscible in the saline aqueous reaction solution. Note that many organic solvents, such as acetone, are miscible in water, but are immiscible, for example, in a saturated aqueous solution of NaCl.

BRIEF DESCRIPTION OF THE FIGURES

FIG. 4A depicts HMF selectivity (%) using a 30 wt % fructose feed. The white bars represent MIBK as the extracting solvent; the grey bars represent 7:3 (w/w) MIBK:2-butanol as the extracting solvent. FIG. 4B depicts the extraction ratio, R, using MIBK (white bars) or 7:3 (w/w) MIBK:2-butanol (grey bars) as the extracting solvent. FIG. 4C depicts HMF selectivity (%) using 7:3 (w/w) MIBK:2-butanol extracting solvent: white bars depict using a 30 wt % fructose feed; grey bars depict using a 50 wt % fructose feed; hatched bars depict the improvement obtained using double the amount of extracting solvent.

Along with HCl, experiments were conducted with $H_2SO_4$ and $H_3PO_4$ at pH 1.5 and 5:5 water:DMSO (w/w) as the aqueous phase and 7:3 MIBK:2-butanol (w/w) as the extracting solvent.

DETAILED DESCRIPTION

Abbreviations and Definitions: The following abbreviations and definitions are used throughout the specification and claims. Words and phrases not explicitly defined herein are to be afforded their standard definition in the art of chemical engineering.

Figure 1A:
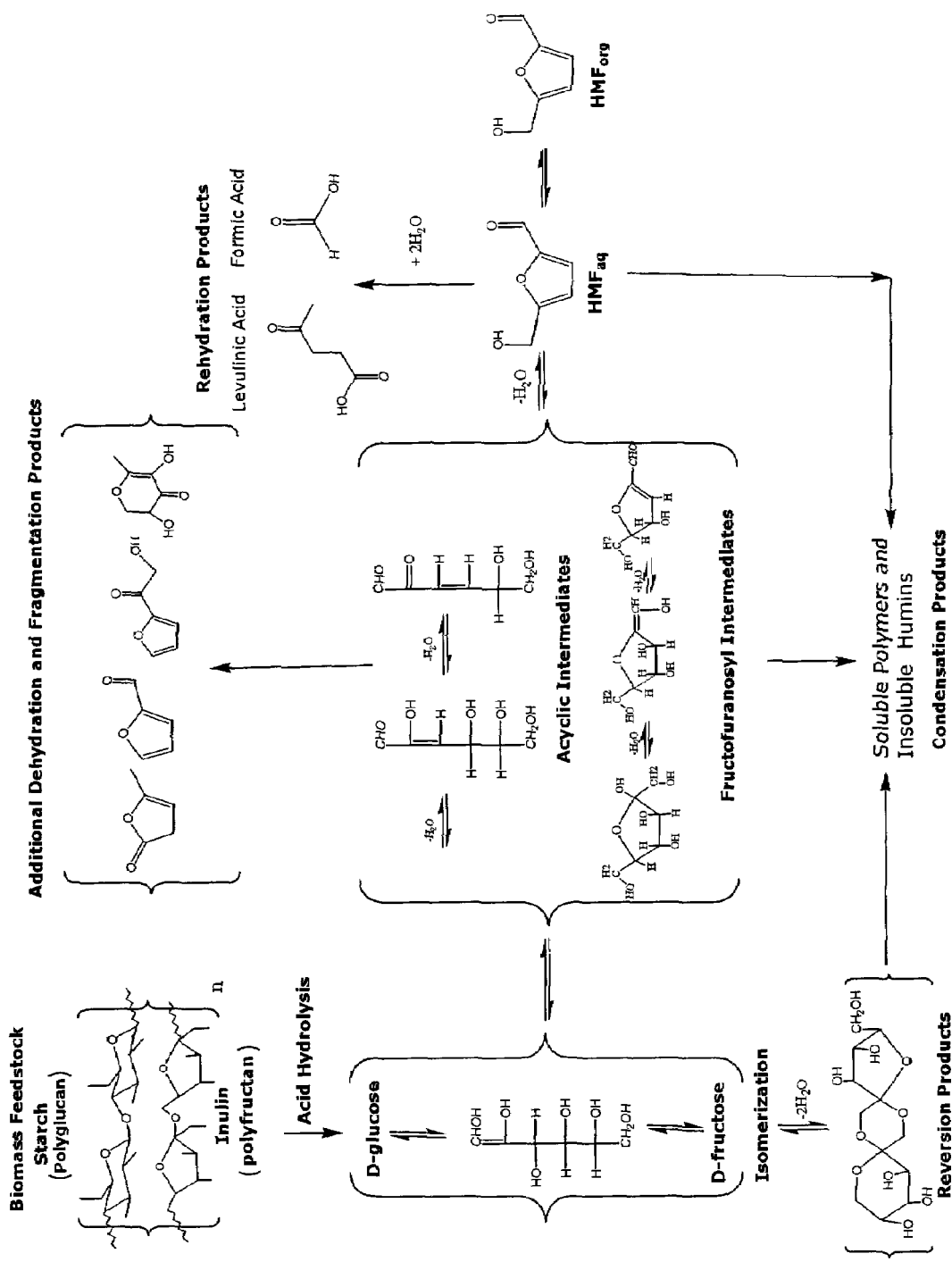
FIG. 1A is a schematic diagram depicting reaction pathways for the acid-catalyzed dehydration of polysaccharides containing hexose monomer units. The structures in brackets correspond to representative species.

1B=NaCl
2B=2-butanol.
Biomass=any plant material, vegetation, or agricultural waste, from any source, that can be used to supply carbohydrates to be used as reactants in the process disclosed herein.
Carbohydrates=Any of a group of organic compounds that includes (without limitation) sugars, starches, celluloses, and gums and serves as a major energy source in the diet of animals. Carbohydrates are produced by photosynthetic plants and contain only carbon, hydrogen, and oxygen atoms.
DCM=dichloromethane.
Dipolar, aprotic additive=a water-soluble compound that: (a) cannot donate labile hydrogen atoms to form strong hydrogen bonds; (b) has a dielectric constant greater than about 15; and (c) has a permanent dipole moment. dimethylformamide, DMSO, NMP, pyrrolidinone, and PVP are examples of dipolar, aprotic additives.
DMF=dimethylfuran.
DMSO=dimethylsulfoxide.
FDCA=2,5-furandicarboxylic acid.
Fur=furfural.
Furan derivative compounds: A compound having the structure:

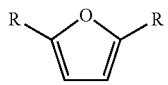

wherein each R is independently selected from the group consisting of hydrogen, $C_1$-$C_6$-alkyl, hydroxy-$C_1$-$C_6$-alkyl, acyl-$C_1$-$C_6$-alkyl, $C_1$-$C_6$-alkylcarbonyl-$C_1$-$C_6$-alkyl, and carboxy-$C_1$-$C_6$-alkyl, and provided the both R's are not simultaneously hydrogen. (Furan itself is the compound where both R groups are hydrogen.) Explicitly included within the phrase "furan derivative" are 5-hydroxymethylfurfural and furfural.
Group VIIIB metal: a metal selected from the group consisting of Fe, Co, Ni, Ru, Rh, Pd, Os, Ir, and Pt.
HMF=5-hydroxymethylfurfural.
MeTHF=methyltetrahydrofuran.
MIBK=methylisobutylketone.
MCM=mobile crystalline materials.
NaCl=sodium chloride
NMP=1-methyl-2-pyrrolidinone.
PBT=polybutyleneterephthalate.
PEG=polyethyleneglycol.
PET=polyethyleneterephthalate.
PVP=poly(1-vinyl-2-pyrrolidinone).
Overview: In the present invention, a carbohydrate, preferably a simple sugar such as glucose, fructose, xylose, and the like, or more complex carbohydrates such as starch, cellobiose, sucrose, inulin, xylan, and the like, is dehydrated, optionally in the presence of an acid catalyst, to produce furan derivatives, such as HMF and various byproducts, as shown in FIG. 1A. FIG. 1A depicts various possible products for a reaction according to the present invention, using polysaccharides with hexose monomer units as the carbohydrate reactant. Although evidence exists supporting both the open-chain and the cyclic fructofuransyl intermediate pathways shown between brackets in FIG. 1A (20, 23), it is clear that the reaction intermediates and the furan derivative products degrade via processes such as fragmentation, condensation, rehydration, reversion, and/or additional dehydration reactions, as shown in FIG. 1A. (Note that FIG. 1A depicts representative reactants, products, and by-products, and is by no means limiting or exhaustive.)

Figure 1B:
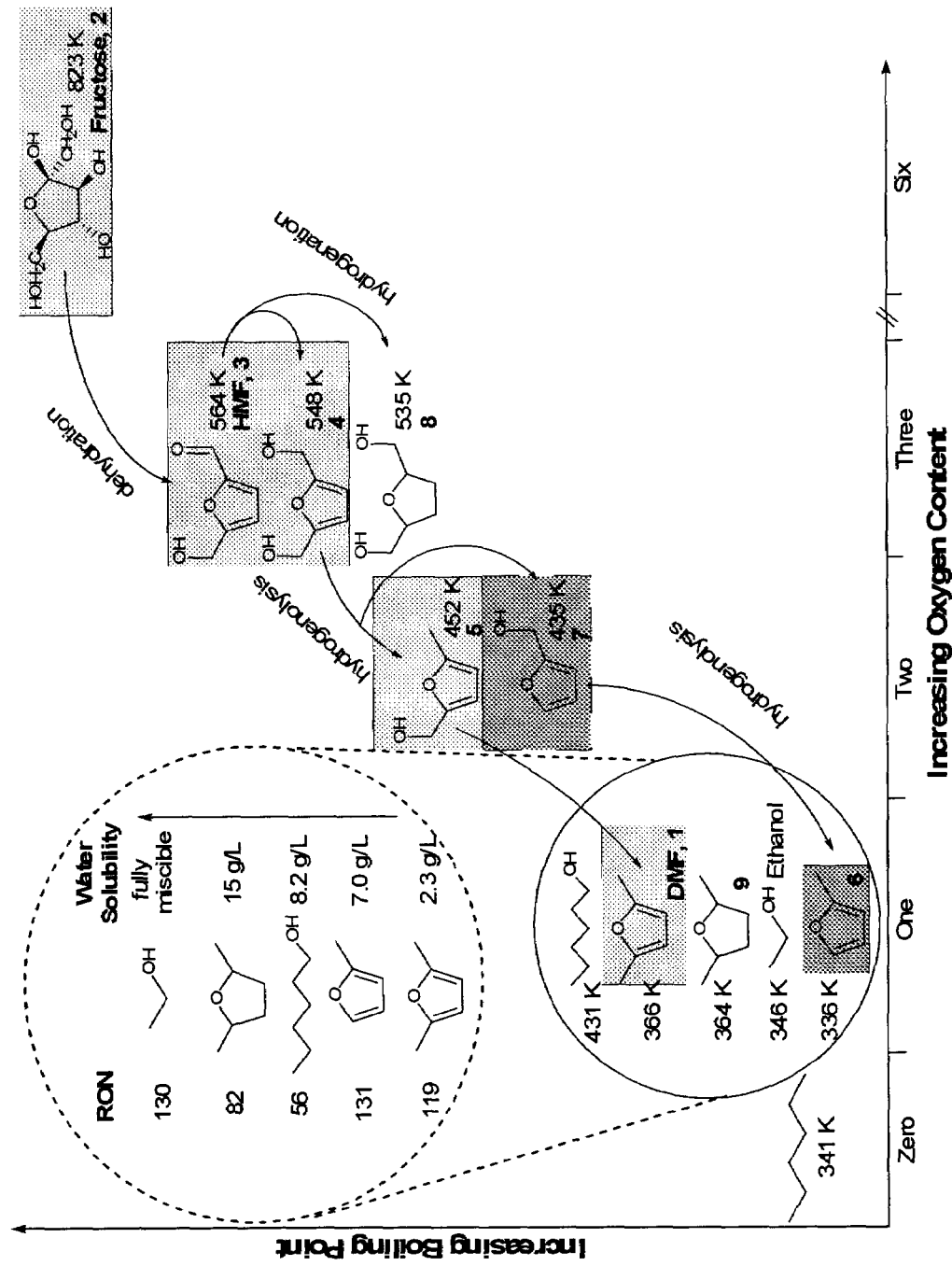
FIG. 1B is a graph depicting the rationale for converting carbohydrates to 2,5-dimethylfuran (DMF). Oxygen content is depicted on the X-axis and boiling point on the Y-axis for each compound shown.

The rationale for converting carbohydrates to 2,5-dimethylfuran (DMF) is outlined in FIG. 1B. The selective removal of five oxygen atoms from a hexose (e.g., fructose, 2) to produce DMF not only decreases the boiling point to a value suitable for liquid fuels, but also attains the lowest water solubility and the highest research octane number of the mono-oxygenated $C_6$ compounds (30), while preserving a high energy density (30 kJ/cm$^3$). This selective removal of oxygen atoms can be accomplished in two steps: (1) removing three oxygen atoms by dehydration to produce 5-hydroxymethylfurfural (HMF); and (2) removing two oxygen atoms by hydrogenolysis to produce DMF via intermediates 4 and 5 as shown in FIG. 1B. Species 6, produced via 7, is a hydrogenolysis byproduct that also possesses excellent fuel qualities.

The present invention is a method of making furan derivative compounds. The method addresses the key furan derivative production limitations using a modified biphasic reaction system. In short, the method of the present invention maximizes production of the desired furan derivative compounds, using any type of carbohydrate (but most preferably simple sugars) as the reactant. Specifically, the present invention is a process that vastly improves the selectivity for furan derivatives such as HMF (defined as the moles of HMF produced divided by the moles of carbohydrate reacted) of an acid-catalyzed dehydration of concentrated (10-50 wt %) carbohydrate feeds by adding modifiers to one or both phases in a biphasic reaction solution (an aqueous reaction phase and a non-aqueous extraction phase). When using specific two-phase systems, most notably when the organic phase is dichloromethane and the aqueous reaction phase is a mixture of water and DMSO, the acid catalyst can be omitted entirely. In this particular biphasic system, furan derivative compounds can be produced at high selectivities and conversion rates without adding an acid catalyst.

In the preferred embodiment, the reactive aqueous phase containing the acid catalyst and the carbohydrate reactant (preferably a sugar) is optionally modified with one or more modifiers consisting of metal salts (preferably NaCl) and/or dipolar, aprotic additives (preferably DMSO and/or 1-methyl-2-pyrrolidinone (NMP)) and/or a hydrophilic polymer (preferably poly(1-vinyl-2-pyrrolidinone) (PVP)). The aqueous-phase-immiscible organic phase (preferably 1-butanol or MIBK) used during the reaction (to extract the furan derivative product) is preferably modified with a $C_1$- to $C_{12}$-alcohol, more preferably a primary or secondary, linear, branched, or cyclic $C_3$- to $C_8$-alkanol, and most preferably 2-butanol. The ratio of relative volumes of the organic and aqueous phases in the reactor ($V_{org}/V_{aq}$), as well as the ratio of the product concentration in the organic layer to that in the aqueous layer (defined as the extraction ratio, R) proved to be important variables in the process (as described below). Upon completion of the dehydration reaction, both phases can be separated for efficient product isolation. Although various acid catalysts can be used to perform the dehydration reaction, HCl is preferred because it showed the highest HMF selectivity of the common mineral acid catalysts (see Table 2, runs 5, 8, and 40-43).

The Reactor: A reactor system suitable for carrying out the present invention is illustrated schematically in FIG. 5 (where the aqueous phase is shown in white and the organic phase in grey). The reactor system includes a biphasic reactor vessel R1, and a solvent evaporator E1. These components (as well as the other components described later) are connected by conventional conduits, which are depicted as arrows or dashed lines in FIG. 5. Any number of conventional valves, pumps, sampling ports, injection ports, etc., explicitly not shown in FIG. 5 for purposes of clarity, may be included in the reactor system to control the flow of feed, reactants, aqueous solvents and additives, organic solvents and additives, and product.

In operation, the reaction of the carbohydrate feed stock takes place in the aqueous phase, at elevated temperatures. The furan derivative product formed (shown as HMF in FIG. 5) is far more soluble in the organic phase than in the aqueous phase and thus is mostly extracted into the organic phase. The small amount of HMF remaining in the aqueous phase is extracted by contacting the aqueous phase with fresh organic solvent. The aqueous phase and solvent are recycled back to the reaction vessel R1. The organic fraction from reactor R1 is transferred to the evaporator E1 where the solvent is removed (thereby leaving the isolated furan derivative product). The evaporated organic solvent is recycled back into the organic portion of the reactor vessel. The resulting isolated furan derivative product is then retrieved from the evaporator.

Thus, the first step in the process comprises an acid-catalyzed dehydration of fructose to produce HMF in a biphasic reactor. Because the normal boiling point of HMF is too high for it to be used as a fuel (see FIG. 1B), the HMF extracted by the organic phase of the biphasic reactor R1 is subsequently converted to DMF by hydrogenolysis of C—O bonds over a metal catalyst, preferably a Group VIIIB metal-containing catalyst (and most preferably a copper-ruthenium (CuRu) catalyst) in reactor R2 as shown in FIG. 5.

Using the inventive method disclosed herein, HMF can be produced in high yields by the acid-catalyzed dehydration of fructose in a biphasic reactor using low boiling point solvents that themselves are excellent fuel components, thereby eliminating the need for expensive separation steps to produce the final liquid fuel mixture. The present method does not require using high boiling point solvents, such as DMSO or mixed solvents containing DMSO, which must be removed from the final product. The reactive aqueous phase in the biphasic reactor contains an acid catalyst and a sugar, and the extracting phase contains a partially miscible organic solvent (e.g., butanol) that continuously extracts the HMF product. Importantly, the addition of a salt to the aqueous phase improves the partitioning of HMF into the extracting phase and leads to increased HMF yields without the use of high boiling point solvents.

Figure 5:
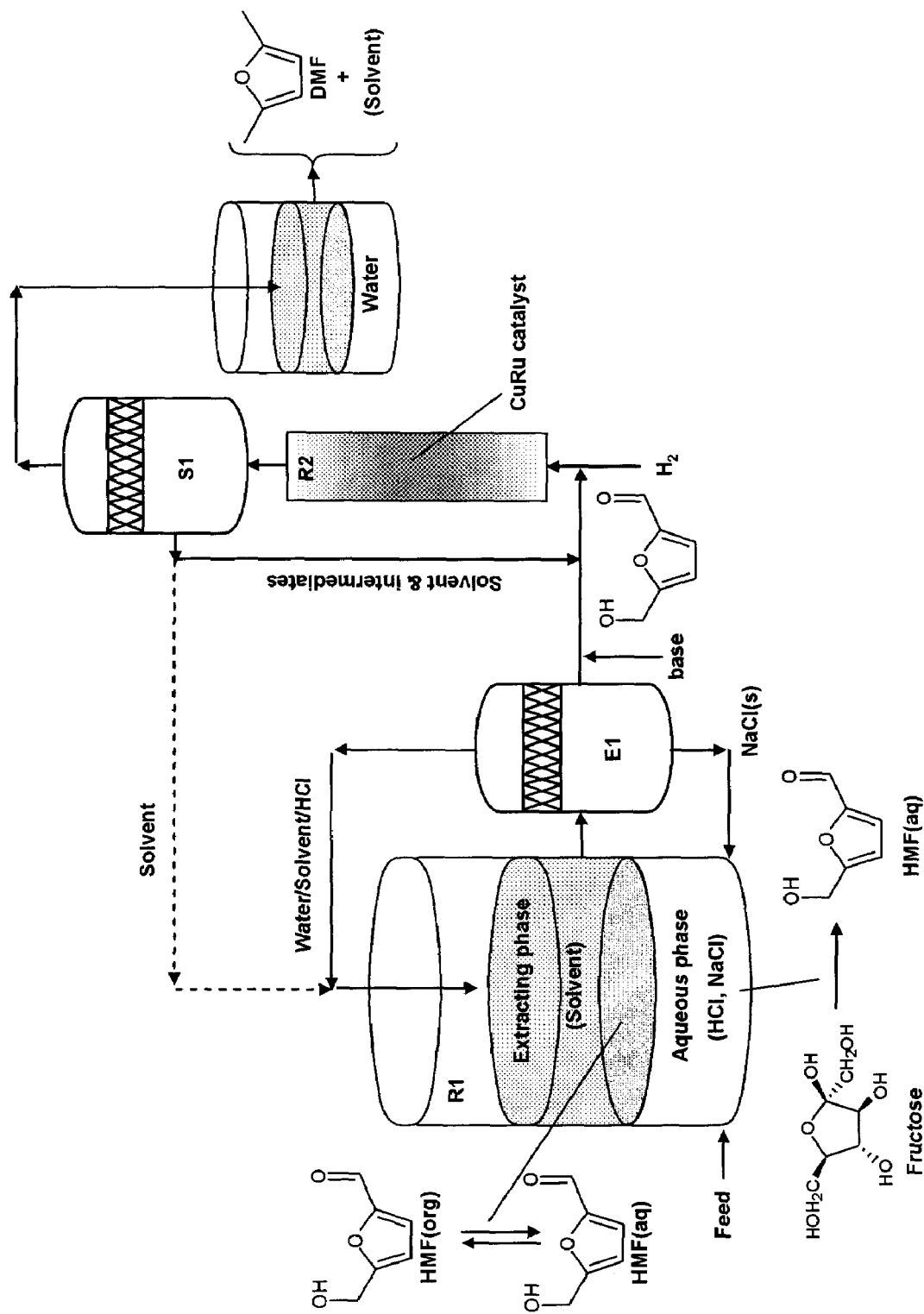
FIG. 5 is a schematic diagram depicting a reactor for producing HMF from fructose, including simulated countercurrent extraction and evaporation apparatus. The aqueous phase (white) containing fructose, the acid catalyst, and the aqueous phase chemical modifiers is represented in the bottom half of the reactor R1. The organic phase (grey) containing the extracting solvent (e.g. 1-butanol or MIBK:2-butanol) is represented in the top half of the reactor R1.

Still referring to FIG. 5, in the aqueous phase within reactor R1, a carbohydrate feed (fructose is shown for illustrative purpose only) is dehydrated in the presence of an acid to yield HMF. Salt is preferably added to the aqueous phase to "salt-out" the resulting HMF into the extracting organic phase. The extracting phase within reactor R1 uses an organic solvent that has the following characteristics: (1) favors extraction of HMF from the aqueous phase; (2) is inert in the subsequent reactions of the product; and (3) facilitates separation of the final DMF product. The evaporator, E1, removes and recycles a fraction of the organic solvent, trace levels of water, and the acid (HCl is shown for illustrative purposes only). Removal of the water yields to precipitation of small amounts of salt that are dissolved in the extracting phase. The precipitate is returned to the aqueous phase of the reactor R1.

In the second part of the reactor, HMF is converted to DMF. $CuCrO_4$ is an effective catalyst for the hydrogenolysis of HMF to DMF, although no studies of this reaction have been reported. The liquid-phase batch experiments of HMF hydrogenolysis using $CuCrO_4$ showed 61% yield (defined as the product of selectivity and conversion) for DMF and 29% yield for 5 (see FIG. 1B for structures that correspond to the compound nos.; see also the Examples for further details). Importantly, however, trace levels of chloride ions in the solvent (introduced during the dehydration step and not completely removed during the evaporation step) deactivate the $CuCrO_4$ catalyst significantly. For instance, when this catalyst is used in a 1-butanol solution containing 1.6 mmol/L of NaCl, only 6% yield of DMF is obtained.

To alleviate poisoning of the copper catalyst, a chloride-resistant carbon-supported copper-ruthenium (CuRu/C) catalyst was developed. The rationale for using this catalyst was that it was observed by the present inventors that a carbon-supported ruthenium catalyst was resistant to deactivation in the presence of chloride ions; however, this catalyst converted HMF primarily to 8. Because copper and ruthenium are immiscible, and copper has a lower surface energy than ruthenium, their mixture creates a two-phase system in which the copper phase coats the surface of the ruthenium phase. Accordingly, it was hypothesized that a CuRu/C catalyst would exhibit copper-like hydrogenolysis behavior combined with ruthenium-like chlorine resistance, which proved to be the case.

Liquid-phase hydrogenolysis experiments using a 3:1 (atomic ratio) Cu:Ru/C catalyst produce yields of 71% DMF, 4% of compound 6, and 12% intermediates. Notably, the same catalyst used with a purified 1-butanol solution containing 1.6 mmol/L of NaCl generates yields of 61% DMF, 4% of compound 6, and 20% intermediates. Thus, although CuRu/C is affected to some extent by the presence of chloride species, its performance is markedly superior to that of $CuCrO_4$.

Alternatively, because NaCl does not evaporate, vapor-phase hydrogenolysis experiments were performed using a flow reactor to eliminate effects of chloride ions on CuRu/C. Vapor-phase hydrogenolysis using a 3:2 Cu:Ru/C catalyst shows yields of 76% to 79% DMF and ~5% intermediates for 1.5 and 10 wt % HMF feeds. No chlorinated hydrocarbons were detected after reaction. Thus, although the vapor-phase process requires vaporization of the feed, it offers multiple benefits. First, when compared to the liquid-phase process, it generates no byproducts and fewer intermediates. Second, it can process both dilute and concentrated HMF solutions. Third, because the same yields were obtained when using 1-butanol or 1-hexanol, other solvents can be used without altering the selectivity. Finally, although the catalyst slowly deactivates after processing an amount of HMF equivalent of 1.7 times the mass of the catalyst, it can be regenerated fully by flowing hydrogen at the reaction temperature.

DMF can optionally be hydrogenated to 9 over a Group VIIIB metal-containing catalyst, preferably a ruthenium-containing catalyst. Compound 9 contains a higher hydrogen to carbon ratio in comparison to DMF, which translates into a higher energy content. Moreover, 9 may provide additional stability upon storage over extended periods of time because it contains a fully hydrogenated furan ring. The toxicological properties of neither DMF nor 9 have been thoroughly tested. The limited information available suggests that DMF is not more toxic than current fuel components.

The final step illustrated in FIG. 5 involves the separation of DMF from the solvent and the reaction intermediates in separator S1. The more volatile components (i.e., DMF, compound 6, and water) can be separated from the solvent and the intermediates; the water can then be recycled back to the hydrogenolysis reactor R2. Upon condensation, the hydrophobic DMF and 6 products separate spontaneously from water. Depending on the final fuel composition requirements, a distillation process may be used to control more precisely the distribution of components and also to recycle a fraction of the solvent to the dehydration reactor. The energy required to evaporate the stream containing DMF and 1-butanol, leading to product separation, is approximately one third of the energy required to evaporate an aqueous solution of ethanol produced by fermentation for biofuel applications.

Feedstock: The feedstocks for use in the present method can comprise any carbohydrate. Thus, for example, suitable feedstocks include hexoses (such as glucose, fructose, mannose, galactose, sorbose, etc.), pentoses (such as xylose, ribose, arabinose, etc.), as well as other mono-, di-, oligo-, and polysaccharides (such as sucrose, inulin, starch, etc.), and lignocellulosic material (such as cellulose, cellobiose, hemicellulose, xylan, etc.).

Aqueous Phase and Aqueous Phase Modifiers: The aqueous layer comprises water or a combination of water and one or more aqueous phase modifiers. The aqueous phase modifiers improve the selectivity and/or reactivity of the reaction toward furan derivatives. Preferably, the aqueous phase modifiers stay in the aqueous phase upon contact with the immiscible extracting layer (or are taken-up only in limited quantities into the extracting layer). The aqueous phase modifiers are generally selected from water-miscible inorganic salts selected from the group consisting of halides, sulfates, sulfides, phosphates, nitrates, acetates, carbonates, and ionic liquids (e.g., 1-butyl-3-methylimidazolium tetrafluoroborate); and/or dipolar, aprotic compounds such as such as sulfoxides (e.g., DMSO), amides (e.g., dimethylformamide), pyrrolidinones (e.g., NMP), nitriles (e.g., acetonitrile), pyrones, lactones (e.g., butyrolactone), water-miscible alcohols or ketones (methanol, ethanol, acetone) and dioxane, and water-soluble polymers such as PVP and PEG. The volume percentage of the aqueous modifier ranges from about 0.1 vol % to saturation for the salts, and from about 5 vol % to about 90 vol % for the aprotic additives so as to create a biphasic system with the organic phase.

Organic Phase and Organic Phase Modifiers: The preferred extractive organic phase for use in the present invention comprises an organic solvent that is immiscible with the chemically modified aqueous phase and (optionally) one or more organic phase modifiers. The preferred organic solvents are 1-butanol, MIBK, and dichloromethane (DCM). Other organic phases, especially other alcohols, ketones, and halogenated alkanes, may also be utilized. Thus, for example, organic solvents such as straight or branched alcohols (e.g. pentanol, tertbutyl alcohol, etc.), straight or branched alkanones (e.g. butanone (i.e., methylethyl ketone), pentanone, hexanone, heptanone, diisobutylketone, 3-methyl-2-butanone, 5-methyl-3-heptanone, etc.), and cycloalkanones (e.g., cyclobutanone, cyclopentanone, cyclohexanone, etc.) may be used in the present invention. Nitriles (such as benzonitrile), aliphatic and cycloaliphatic ethers (e.g., dichloroethylether, dimethyl ether), saturated and unsaturated aliphatic or aromatic hydrocarbons (decane, toluene, benzene), oxygenated hydrocarbons (eg THF, furan, etc.), and nitroalkanes (e.g., nitromethane, nitropropane, etc.) may also be used. Likewise, halogenated derivatives of the above-noted compounds, as well as other halogenated alkanes may also be used as the organic phase (e.g., chloromethane, trichloromethane, trichloroethane, and the like).

The organic phase modifiers are compounds that increase the extracting capability and/or selectivity towards furan derivative compounds. Because they are mostly immiscible in water (at least in the presence of a third component), they partition into the extracting layer and remain mostly in the extracting layer upon contact with the aqueous layer. Suitable organic phase modifiers are selected from the group consisting of $C_1$- to $C_8$-aliphatic alcohols, the most preferred being 2-butanol. The volume percentage of organic phase modifier ranges from about 5 to about 90% so as to create a biphasic system with aqueous phase.

Acid Catalysts: In the preferred embodiment using 1-butanol or MIBK as the extracting solvent, an acid catalyst should be used. The acid catalyst is preferably an inorganic acid, most preferably a mineral acid such as HCl, $HNO_3$, $H_2SO_4$, $H_3PO_4$, $H_3BO_3$, etc. Organic acids (e.g., oxalic acid, levulinic acid, citric acid, etc.), zeolites (Si/Al from 1 to 100), acid and super-acid resins (e.g., cation exchange resin), phosphates ($NbOPO_4$, vanadium phosphate) solid silica-, silica-alumina, and titania-based supports functionalized by acid groups, and other Lewis acids may also be used.

Illustrative Protocols: Experiments with different aqueous- and organic-phase modifiers demonstrate the utility and functionality of the inventive method (see Tables 1 and 2; and FIGS. 2, 3, and 4A, 4B, and 4C) (24). Separate sets of experiments were carried out for different aqueous-phase modifiers (salt-based vs. aprotic-solvent-based) in order to independently demonstrate the utility of each type.

Figure 2:
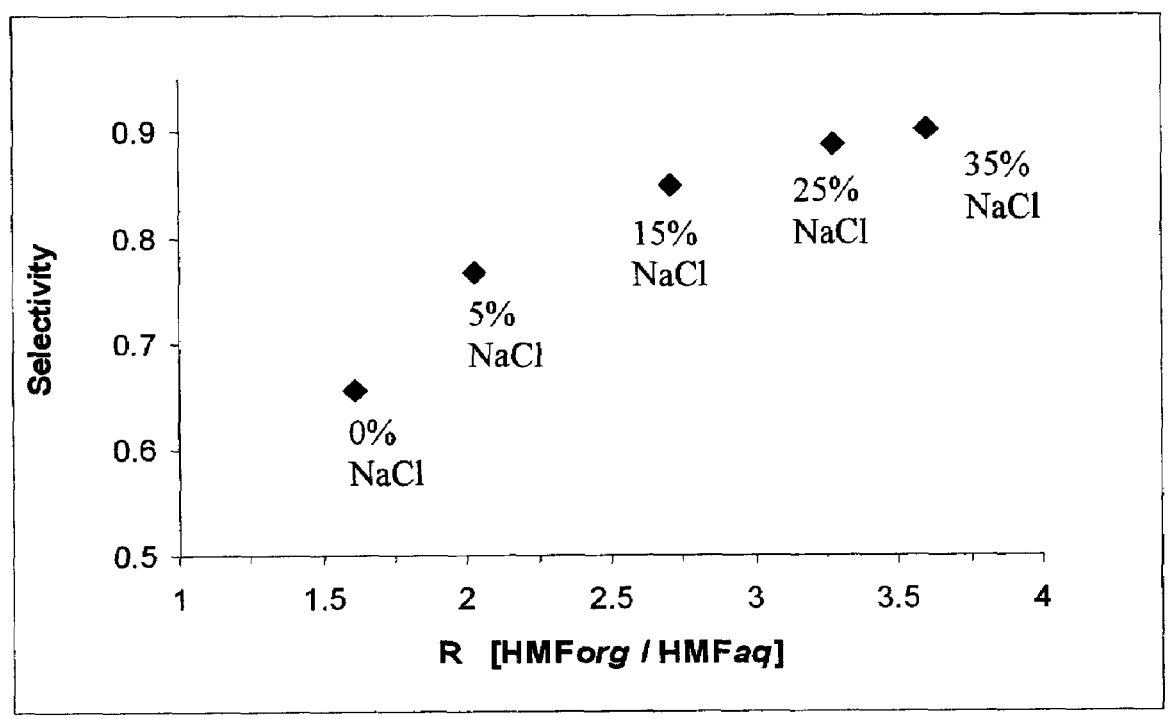
FIG. 2 is a graph depicting the effect of salt content (NaCl) in the aqueous phase on the extraction ratio R and HMF selectivity when practicing present invention using as a feedstock 30 wt % fructose and using 2-butanol as the extracting solvent.
Figure 3:
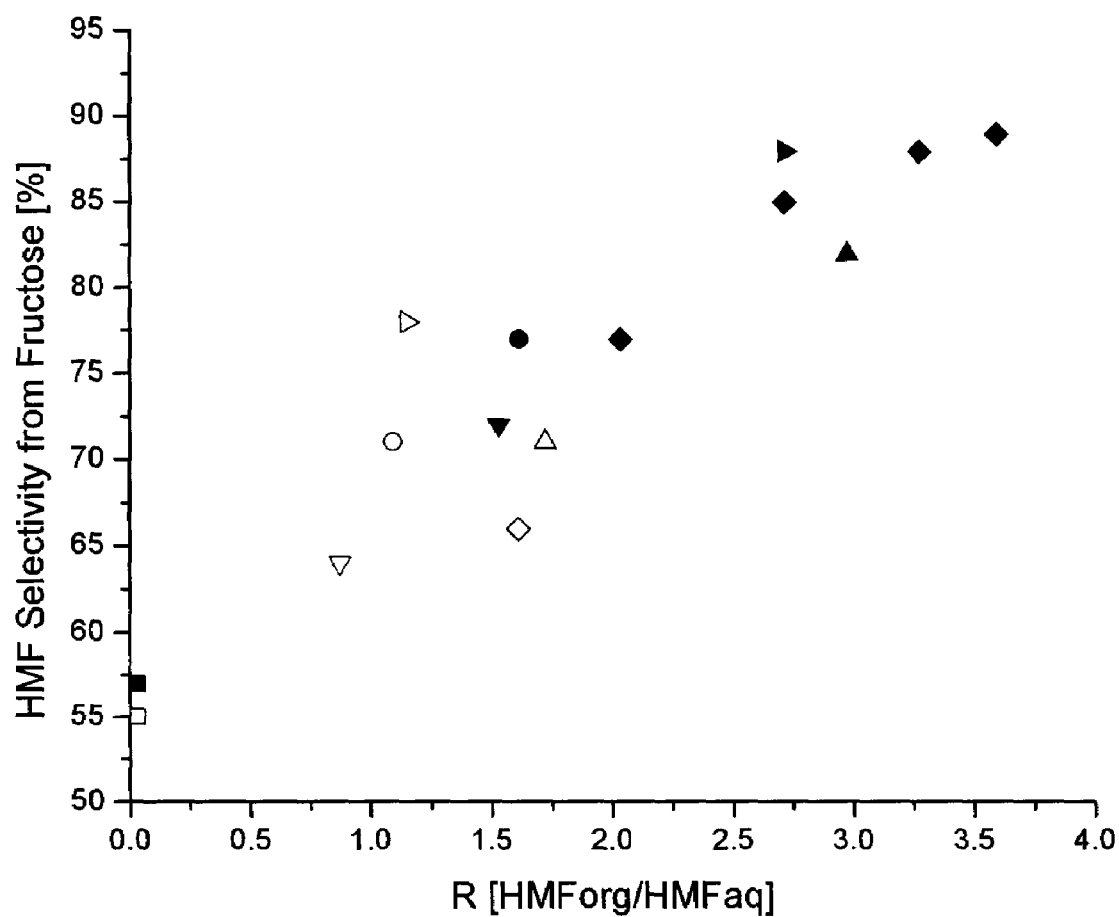
FIG. 3 is a graph depicting the effect of extraction ratio R on HMF selectivity from 30 wt % fructose feeds for various organic solvents. Open symbols correspond to experiments without NaCl and closed symbols correspond to experiments with an aqueous phase saturated with NaCl. Solvent legend: 2-butanol (♦, ◊) (closed diamonds refer to experiments using 2-butanol as the extracting solvent and aqueous phases containing 5, 15, 25, and 35% NaCl; the open diamond refers to an experiment using 2-butanol with no salt and a $V_{org}/V_{aq}$=1.6), 1-butanol (▲, △), 1-hexanol (▼, ▽), MIBK (●, ○), 5:5 toluene:2-butanol (▶, ▷), No solvent (■, □).

Experiments with the salt-based modifiers demonstrate that adding salt to the reactive aqueous phase increases the extracting ratio R (the ratio of the HMF concentration in the organic layer to that in the aqueous layer) by means of the salting-out effect. The salting-out effect is a phenomenon wherein electrolytes alter the intermolecular bonding interactions between liquid components, thereby decreasing the mutual solubility of the aqueous and organic phases. This results in an increased two-phase envelope. The capacity of the organic phase to extract HMF from the reactive aqueous phase, as measured by R, directly affects HMF selectivity. (See FIG. 2.) FIG. 2 is a graph depicting R on the X-axis and selectivity toward HMF on the Y-axis for a series of reactions according to the present invention containing increasing concentrations of salt in the aqueous phase. The results shown in FIG. 2 demonstrate that HMF selectivity increases as the value of R increases, irrespective of the extracting solvent utilized. In turn, these results clearly show that efficiently removing HMF from the aqueous phase prevents undesired side reactions arising from extended HMF residence in the reactive aqueous phase. (See also FIG. 3.) Thus, the value of R for a specific extracting solvent depends not only on the affinity of the solvent for HMF, but also on the ability of the salt to increase the two-phase envelope of the specific system. For example, as compared to experiments without salt, a 30 wt % fructose solution saturated with NaCl (35 g of NaCl/100 g of $H_2O$) using 2-butanol as the extracting solvent (with initial ratio of organic and aqueous phase volumes $V_{org}/V_{aq}$=1.6) results in an increase in R from 1.6 to 3.3, leading to an improvement in HMF selectivity from 66% to 79% (Table 1, Runs 1 and 6). Notably, the presence of NaCl has the additional benefit of allowing higher values of $V_{org}/V_{aq}$ to be utilized, thus leading to higher HMF selectivities, while maintaining biphasic reaction conditions. Specifically, when the ratio $V_{org}/V_{aq}$ is doubled, the 2-butanol system without salt becomes monophasic, while the system saturated with NaCl remains biphasic, with an R of 3.6 and an HMF selectivity of 89% (Table 1, Run 5). The primary role of NaCl is to alter the solvent properties (i.e., to increase R and to widen the two-phase envelope) while otherwise remaining inert. In other words, the dehydration of fructose in the presence of NaCl, but in the absence of an extracting solvent, leads to the same HMF selectivity as in the absence of NaCl (see Table 1, Runs 19 and 20).

Experiments with aprotic, solvent-based modifiers demonstrate that these additives increase the reaction selectivity toward HMF. For 30 wt % fructose feeds, adding the aprotic solvent DMSO increases the HMF selectivity from 60% to 67% when MIBK is used as the extracting solvent. See FIG. 4A. Other aprotic solvents, such as NMP, also have positive effects on HMF selectivity during the dehydration reaction. The dehydration of 10 wt % fructose in 7:3 Water:NMP using MIBK as the extracting solvent and an acidic ion-exchange resin catalyst generated 68% HMF selectivity at 80% conversion. Similarities in the properties of DMSO and NMP seem to indicate that NMP acts via similar mechanisms as DMSO to enhance HMF selectivity in the fructose dehydration reaction. However, while the carryover of DMSO from the aqueous phase into the organic phase is small (<0.8 wt % DMSO in MIBK after contacting an 8:2 water:DMSO aqueous solution as measured by HPLC), the carryover of NMP into the organic phase is considerably higher (~5 wt % NMP in MIBK after contacting a 7:3 water:NMP aqueous solution as measured by HPLC). The relatively large amount of NMP in the organic phase is a factor that must be taken into account in the subsequent separation of HMF from the organic phase by evaporation. Importantly, it was found that replacing NMP with PVP, a stable hydrophilic polymer that has NMP moieties along the polyethylene chain, preserves the benefits on selectivity produced by NMP, but eliminates organic phase contamination due to the low solubility of PVP in the extracting solvent. While aprotic, solvent-based additives increase the specificity of the reaction toward HMF, they also tend to decrease the R value. In short, on the one hand, they primarily increase the rate of fructose conversion into HMF. To some extent, aprotic, solvent-based additives also decrease the rates of undesirable parallel reactions occurring in the aqueous phase; on the other hand, unlike salt-based additives, aprotic, solvent-based additives increase the solubility of HMF in the aqueous phase. That is, these aprotic additives tend to lower the R value. See FIG. 4B.

Figure 4A:
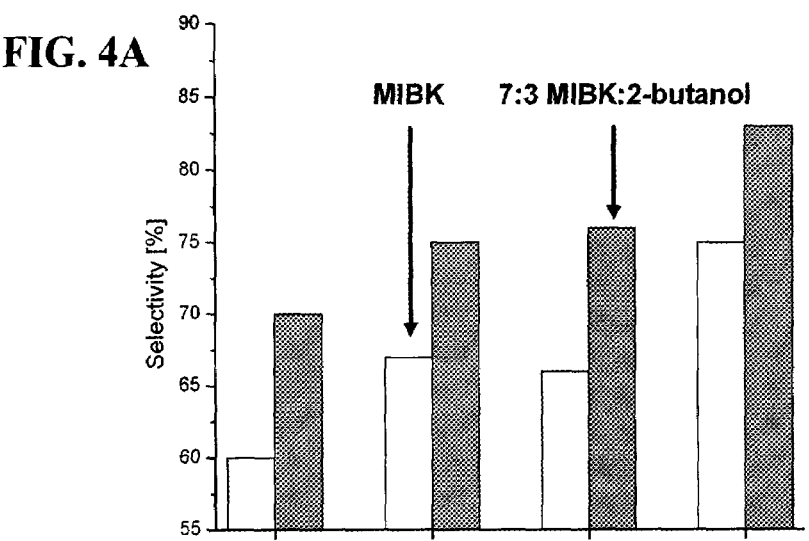
FIGS. 4A, 4B, and 4C are graphs depicting the effects of changing the aqueous phase composition from water ("W"), to 8:2 water:DMSO (w/w) ("W:D"), to 7:3 water:PVP (w/w) ("W:P"), to 7:3 (8:2 water:DMSO):PVP (w/w) (W:D:P).
Figure 4B:
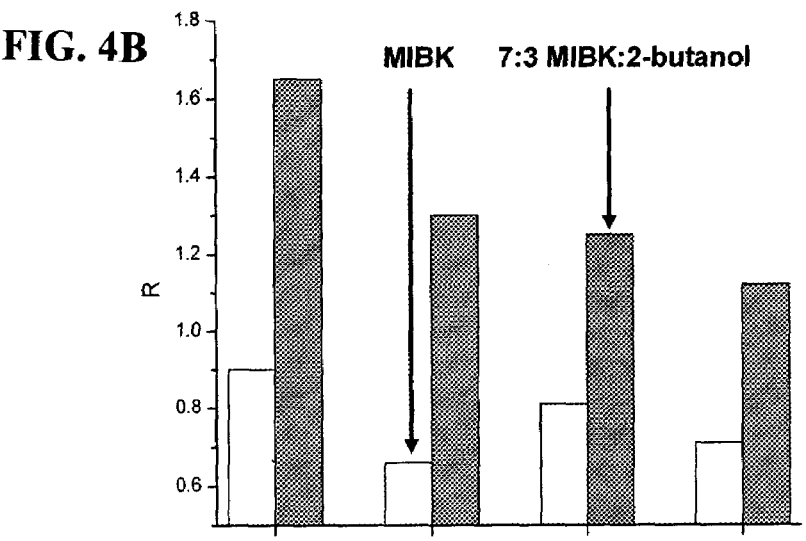
Figure 4C:
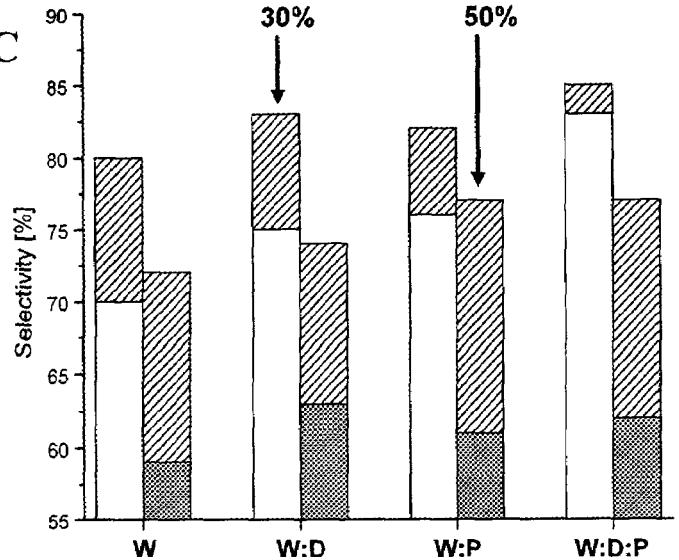

Adding 2-butanol to MIBK as an organic phase modifier helped counter this effect by improving the partitioning of the HMF product into the organic phase (see FIG. 4B). Starting with a 30 wt % aqueous fructose solution and a $V_{org}/V_{aq}$=3.2, the optimal results using all modifiers (DMSO, PVP, and 2-butanol) yielded 0.065 g/ml of HMF in the organic layer, with 83% HMF selectivity at 82% conversion (see Table 2, run 13).

Increasing the extraction ratio R by using suitable modifiers in the aqueous and organic phases (e.g., metal salts and/or 2-butanol), and/or increasing $V_{org}/V_{aq}$, counteract the faster rate of HMF degradation in the presence of fructose. This undesirable reaction between fructose and HMF is reflected in lower HMF selectivities at 50 wt % fructose as compared to 30 wt % (see FIG. 4C and Table 2). It has been observed directly that lower selectivities are obtained when controlled amounts of HMF are added initially to the fructose reaction system. In addition, separating HMF from the aqueous medium lowers the rate of HMF rehydration into levulinic and formic acids. Analyses by GC-MS of the aqueous and organic phases after conversion of 30 wt % fructose showed that the general composition of the byproducts corresponds (typically) to 10% rehydration, 5% dehydration, 5% fragmentation, and 80% condensation compounds.

Simulations were performed for selected experiments from Table 1 to estimate the HMF concentrations that would be obtained by combining the batch reactor experiments described here (and in the Examples) with a counter-current extractor to remove the HMF remaining in the aqueous layer (FIG. 5). The final amount of HMF obtained by combining the organic streams from the reactor and the extractor (i.e., the stream entering the evaporator as shown in FIG. 5) is used to calculate the energetic yield (Yη) as a measure of the overall efficiency of the present process for obtaining HMF by solvent evaporation. The energetic yield is the product of the HMF yield (Y), defined as the moles of HMF in the stream entering the evaporator in FIG. 5 divided by the total moles of fructose fed to the batch reactor, and an energy efficiency (η), defined as the heat of combustion of the HMF product ($\Delta H_{C,HMF}$) minus the energy necessary to evaporate the solvent ($\Delta H_{vap,org}$), normalized by the energy content of the product (i.e., $\eta=(\Delta H_{C,HMF}-\Delta H_{vap,org})/\Delta H_{C,HMF}$). To model a countercurrent extractor operating with equal volumes of aqueous and organic streams, the simulations used: (a) the experimental selectivity for each system (from Tables 1 and 2) (which were assumed to remain constant at 90% conversion); (b) the experimental value of $V_{org}/V_{aq}$ for the batch reactor; and (c) the experimental value of R. It is seen in Table 3 that aqueous and organic phase modifiers improve the value of Yη, thus reducing energy expenditures required to obtain the HMF product when compared to the water/MIBK system.

The value of Yη alone does not address the difficulties of using high-boiling organic systems. For example, although a theoretical value of Yη>75% can be obtained using pure DMSO, the HMF product cannot be separated from DMSO by simple evaporation. (Previous work has shown that because of the reactive nature of concentrated HMF at high temperatures, distillation of HMF from DMSO leads to significant carbonization of the product (10)). Low temperature separation processes such as vacuum evaporation and vacuum distillation have been used to separate various solvents and byproducts from HMF mixtures, but no experimental data have been reported for DMSO (27-29).

Accordingly, in the present work, Aspen Plus simulation software (Version. 12.1, AspenTech, Inc.) was used to compare energy requirements for the separating HMF from a low-boiling solvent (pure MIBK) and from a high-boiling solvent (pure DMSO) for vacuum evaporation and vacuum distillation processes (for HMF levels of 0.1 w/w). Vacuum evaporation simulations predicted that 99.5% of the MIBK solvent can be evaporated at 13 mbar and 343 K with a 2.5% loss of HMF, whereas evaporating DMSO at 1.3 mbar and the same temperature resulted in a 30% loss of HMF (data not shown). Consequently, HMF separation from DMSO with minimal losses requires the more expensive vacuum distillation process (e.g., 0.66 mbar and a bottoms temperature of 386 K). When comparing both solvents using vacuum distillation, simulations predicted that an efficient separation of HMF from pure DMSO requires 40% more energy as compared to pure MIBK, clearly showing the advantages of using a low-boiling solvent system.

TABLE 1

Dehydration results for 30 wt % fructose solutions. Fructose weight percent calculated on a salt-free basis. Standard reaction conditions: T = 453K and $V_{org}/V_{aq}$ = 3.2 with 0.25 M HCl catalyst (mol HCl/L of aqueous phase).

| Run | Salt % | Organic phase | Conversion (%) | Selectivity (%) | [HMF]aq (g/L) | [HMF]org (g/L) | R | [Salt]org (g/L) | [H$_2$O]org (wt %) |
|---|---|---|---|---|---|---|---|---|---|
| 1 | 0%[†] | 2-butanol | 58% | 66% | 28.6 | 46.0 | 1.6 | 0.0 | 31.4% |
| 2 | 5% | | 65% | 77% | 16.8 | 34.1 | 2.0 | 0.9 | 16.4% |
| 3 | 15% | | 65% | 85% | 12.7 | 34.4 | 2.7 | 1.1 | 9.6% |
| 4 | 25% | | 75% | 88% | 11.6 | 37.9 | 3.3 | 1.2 | 6.8% |
| 5 | 35% | | 74% | 89% | 10.6 | 38.1 | 3.6 | 1.6 | 6.5% |
| 6 | 35%[†] | | 71% | 79% | 18.0 | 60.0 | 3.3 | 1.6 | 7.4% |
| 7 | 0% | 1-butanol | 52% | 71% | 15.1 | 26.0 | 1.7 | 0.0 | 23.1% |
| 8 | 35% | | 85% | 82% | 13.2 | 39.2 | 3.0 | 1.6 | 6.1% |
| 9 | 35%[a] | | 80% | 83% | 12.0 | 39.0 | 3.3 | 1.6 | 6.1% |
| 10 | 35%[a] | | 88% | 82% | 12.9 | 43.1 | 3.3 | 1.6 | 6.1% |
| 11 | 35%[a] | | 77% | 84% | 12.4 | 37.8 | 3.0 | 1.6 | 6.1% |
| 12 | 35%[a] | | 64% | 84% | 10.2 | 32.4 | 3.2 | 1.6 | 6.1% |
| 13 | 0% | 1-hexanol | 50% | 64% | 21.1 | 18.4 | 0.9 | 0.0 | 7.9% |
| 14 | 35% | | 78% | 72% | 19.5 | 29.9 | 1.5 | 0.9 | 2.2% |
| 15 | 0% | MIBK | 50% | 71% | 20.0 | 21.8 | 1.1 | 0.0 | 0.9% |
| 16 | 35% | | 72% | 77% | 18.3 | 29.3 | 1.6 | 0.2 | 0.0% |
| 17 | 0% | 5:5 Toluene:2-butanol | 64% | 78% | 27.7 | 31.7 | 1.2 | 0 | 6.7% |
| 18 | 35% | | 74% | 88% | 13.8 | 37.4 | 2.7 | 0.8 | 1.9% |
| 19 | 0% | None | 44% | 55% | 53.5 | 0.0 | 0.0 | 0.0 | — |
| 20 | 35% | | 59% | 57% | 70.8 | 0.0 | 0.0 | 35.0 | — |
| 21 | 5%[††] | 2-butanol | 30% | 36% | 1.2 | 2.3 | 1.9 | 0.9 | 16.4% |
| 22 | 35%[††] | | 56% | 48% | 1.1 | 3.9 | 3.6 | 1.6 | 6.5% |

[a]Runs 9-12 used 0.12, 0.06, 0.03, and 0.01 M HCl, respectively. Error analysis of dehydration experiments based on the 1-butanol and 2-butanol systems saturated with NaCl showed standard deviations in selectivity of ±1.3% and ±1.5%, respectively (5 replicates).
Symbol [†]indicates runs that used $V_{org}/V_{aq}$ = 1.6.
Symbol [††]indicates a run that used a 10 wt % glucose (salt-free basis) feed. Salt % is expressed as grams of salt divided by grams of water × 100.

TABLE 2

Results for acid-catalyzed dehydration of fructose. Runs 1-27 were carried out at 453K for 2.5-3 minutes using 0.25 M HCl aqueous phase solutions; runs 28-39 were carried out at 363K for 8-16 hours using an acidic ion-exchange resin at a 1:1 w/w fructose:resin ratio. Aqueous phase and organic phase compositions are reported as w/w ratios. Conversion is defined as the ratio of fructose consumed to fructose added initially. R = [HMF]$_{org}$/[HMF]$_{aq}$. Standard runs for HCl, H$_2$SO$_4$ and H$_3$PO$_4$ catalysts used 1.5 g of aqueous phase and 1.5 g of extracting solvent. Runs marked with * used 3 g of extracting solvent. Runs for resin catalyst used 5.0 g of aqueous phase and 5.0 g of extracting solvent. $V_{org}/V_{aq}$ measured upon completion of reaction.

| Run # | Aqueous Phase Composition | Organic Phase Composition | Conversion (%) | Selectivity (%) | [HMF]$_{aq}$ (g/ml) | [HMF]$_{org}$ (g/ml) | R | $V_{org}/V_{aq}$ |
|---|---|---|---|---|---|---|---|---|
| | | 30 wt % fructose with HCl catalyst | | | | | | |
| 1 | Water | none | 50 | 51 | 0.060 | — | 0.00 | 0.00 |
| 2 | Water | MIBK | 91 | 60 | 0.056 | 0.050 | 0.90 | 1.51 |
| 3* | Water | MIBK | 75 | 73 | 0.035 | 0.033 | 0.96 | 3.13 |
| 4 | Water | 7:3 MIBK:2-butanol | 68 | 70 | 0.033 | 0.054 | 1.65 | 1.56 |
| 5* | Water | 7:3 MIBK:2-butanol | 86 | 80 | 0.026 | 0.045 | 1.73 | 3.68 |
| 6 | 8:2 Water:DMSO | MIBK | 94 | 67 | 0.077 | 0.050 | 0.66 | 1.41 |
| 7 | 8:2 Water:DMSO | 7:3 MIBK:2-butanol | 80 | 75 | 0.050 | 0.064 | 1.30 | 1.49 |
| 8* | 8:2 Water:DMSO | 7:3 MIBK:2-butanol | 87 | 82 | 0.034 | 0.046 | 1.39 | 3.65 |
| 9 | 7:3 Water:PVP | MIBK | 74 | 66 | 0.055 | 0.041 | 0.81 | 1.56 |
| 10 | 7:3 Water:PVP | 7:3 MIBK:2-butanol | 62 | 76 | 0.042 | 0.047 | 1.25 | 1.57 |
| 11* | 7:3 Water:PVP | 7:3 MIBK:2-butanol | 79 | 82 | 0.030 | 0.041 | 1.44 | 3.83 |
| 12 | 7:3 (8:2 Water:DMSO):PVP | MIBK | 79 | 75 | 0.071 | 0.047 | 0.71 | 1.52 |
| 13 | 7:3 (8:2 Water:DMSO):PVP | 7:3 MIBK:2-butanol | 82 | 83 | 0.063 | 0.065 | 1.12 | 1.62 |
| 14* | 7:3(8:2 Water:DMSO):PVP | 7:3 MIBK:2-butanol | 89 | 85 | 0.043 | 0.046 | 1.17 | 3.99 |
| | | 50 wt % fructose with HCl catalyst | | | | | | |
| 15 | Water | none | 51 | 28 | 0.064 | — | 0.00 | 0.00 |
| 16 | Water | MIBK | 65 | 47 | 0.049 | 0.051 | 1.11 | 1.80 |
| 17 | Water | 7:3 MIBK:2-butanol | 71 | 59 | 0.049 | 0.079 | 1.73 | 1.91 |
| 18* | Water | 7:3 MIBK:2-butanol | 88 | 72 | 0.045 | 0.069 | 1.55 | 4.66 |
| 19 | 8:2 Water:DMSO | MIBK | 71 | 57 | 0.076 | 0.060 | 0.86 | 1.69 |
| 20 | 8:2 Water:DMSO | 7:3 MIBK:2-butanol | 80 | 63 | 0.077 | 0.085 | 1.19 | 1.87 |

TABLE 2-continued

Results for acid-catalyzed dehydration of fructose. Runs 1-27 were carried out at 453K for 2.5-3 minutes using 0.25 M HCl aqueous phase solutions; runs 28-39 were carried out at 363K for 8-16 hours using an acidic ion-exchange resin at a 1:1 w/w fructose:resin ratio. Aqueous phase and organic phase compositions are reported as w/w ratios. Conversion is defined as the ratio of fructose consumed to fructose added initially. R = $[HMF]_{org}/[HMF]_{aq}$. Standard runs for HCl, $H_2SO_4$ and $H_3PO_4$ catalysts used 1.5 g of aqueous phase and 1.5 g of extracting solvent. Runs marked with * used 3 g of extracting solvent. Runs for resin catalyst used 5.0 g of aqueous phase and 5.0 g of extracting solvent. $V_{org}/V_{aq}$ measured upon completion of reaction.

| Run # | Aqueous Phase Composition | Organic Phase Composition | Conversion (%) | Selectivity (%) | $[HMF]_{aq}$ (g/ml) | $[HMF]_{org}$ (g/ml) | R | $V_{org}/V_{aq}$ |
|---|---|---|---|---|---|---|---|---|
| 21* | 8:2 Water:DMSO | 7:3 MIBK:2-butanol | 91 | 74 | 0.059 | 0.072 | 1.30 | 4.87 |
| 22 | 7:3 Water:PVP | MIBK | 85 | 56 | 0.074 | 0.060 | 0.80 | 1.72 |
| 23 | 7:3 Water:PVP | 7:3 MIBK:2-butanol | 77 | 61 | 0.076 | 0.081 | 1.19 | 1.85 |
| 24* | 7:3 Water:PVP | 7:3 MIBK:2-butanol | 90 | 77 | 0.062 | 0.070 | 1.22 | 5.15 |
| 25 | 7:3(8:2 Water:DMSO):PVP | MIBK | 77 | 61 | 0.095 | 0.066 | 0.77 | 1.85 |
| 26 | 7:3(8:2 Water:DMSO):PVP | 7:3 MIBK:2-butanol | 72 | 62 | 0.068 | 0.074 | 1.25 | 1.89 |
| 27* | 7:3(8:2 Water:DMSO):PVP | 7:3 MIBK:2-butanol | 92 | 77 | 0.076 | 0.070 | 1.03 | 5.11 |
| | 10 wt % fructose with ion-exchange resin catalyst | | | | | | | |
| 28 | Water | MIBK | 75 | 44 | 0.010 | 0.011 | 1.02 | 1.32 |
| 29 | Water | MIBK | 17 | 43 | 0.002 | 0.002 | 1.15 | 1.29 |
| 30 | Water | 7:3 MIBK:2-butanol | 61 | 60 | 0.009 | 0.014 | 1.61 | 1.31 |
| 31 | 8:2 Water:DMSO | MIBK | 84 | 47 | 0.015 | 0.012 | 0.79 | 1.26 |
| 32 | 8:2 Water:DMSO | MIBK | 19 | 80 | 0.005 | 0.004 | 0.87 | 1.24 |
| 33 | 8:2 Water:DMSO | 7:3 MIBK:2-butanol | 74 | 68 | 0.015 | 0.017 | 1.18 | 1.24 |
| 34 | 7:3 Water:PVP | MIBK | 74 | 63 | 0.018 | 0.013 | 0.79 | 1.43 |
| 35 | 7:3 Water:PVP | 7:3 MIBK:2-butanol | 70 | 65 | 0.015 | 0.015 | 1.04 | 1.46 |
| 36 | 7:3(8:2 Water:DMSO):PVP | MIBK | 80 | 71 | 0.026 | 0.013 | 0.54 | 1.38 |
| 37 | 7:3(8:2 Water:DMSO):PVP | 7:3 MIBK:2-butanol | 76 | 77 | 0.020 | 0.019 | 1.03 | 1.43 |
| | 30 wt % fructose with ion-exchange resin catalyst | | | | | | | |
| 38 | 7:3(8:2 Water:DMSO):PVP | MIBK | 89 | 60 | 0.066 | 0.041 | 0.66 | 1.65 |
| 39 | 7:3(8:2 Water:DMSO):PVP | 7:3 MIBK:2-butanol | 83 | 65 | 0.053 | 0.051 | 1.07 | 1.74 |
| | 30 wt % fructose with $H_2SO_4$ catalyst | | | | | | | |
| 40* | Water | 7:3 MIBK:2-butanol | 80 | 66 | 0.022 | 0.035 | 1.63 | 3.54 |
| 41* | 8:2 Water:DMSO | 7:3 MIBK:2-butanol | 85 | 71 | 0.029 | 0.040 | 1.35 | 3.59 |
| | 30 wt % fructose with $H_3PO_4$ catalyst | | | | | | | |
| 42* | Water | 7:3 MIBK:2-butanol | 65 | 65 | 0.016 | 0.029 | 1.89 | 3.47 |
| 43* | 8:2 Water: DMSO | 7:3 MIBK:2-butanol | 51 | 76 | 0.016 | 0.025 | 1.58 | 2.95 |

TABLE 3

Simulation of HMF yield (Y) and energetic yield (Yη) for selected dehydration systems. $[HMF]_{aq}$ corresponds to the HMF concentration in the aqueous phase leaving the extractor, and $[HMF]_{org}$ corresponds to the HMF concentration entering the evaporator in FIG. 3.

| Run* # | Aqueous Phase Composition | Organic Phase Composition | Selectivity† (%) | $[HMF]_{aq}$ (g/ml) | $[HMF]_{org}$ (g/ml) | Y‡ (%) | Yη (%) |
|---|---|---|---|---|---|---|---|
| | | 30 wt % fructose | | | | | |
| 2 | Water | MIBK | 60 | 0.007 | 0.045 | 48 | 34 |
| 4 | Water | 7:3 MIBK:2-butanol | 70 | 0.0001 | 0.057 | 61 | 43 |
| 6 | 8:2 Water:DMSO | MIBK | 67 | 0.025 | 0.048 | 48 | 35 |
| 7 | 8:2 Water:DMSO | 7:3 MIBK:2-butanol | 75 | 0.001 | 0.063 | 66 | 48 |
| 12 | 7:3(8:2 Water:DMSO):PVP | MIBK | 75 | 0.024 | 0.057 | 56 | 44 |
| 13 | 7:3(8:2 Water:DMSO):PVP | 7:3 MIBK:2-butanol | 83 | 0.003 | 0.071 | 73 | 56 |
| | | 50 wt % fructose | | | | | |
| 16 | Water | MIBK | 47 | 0.00260 | 0.05381 | 39 | 27 |
| 26 | 7:3(8:2 Water:DMSO):PVP | MIBK | 62 | 0.00186 | 0.09079 | 53 | 43 |
| 27 | 7:3(8:2 Water:DMSO):PVP | 7:3 MIBK:2-butanol | 77 | 0.00552 | 0.07102 | 67 | 51 |

*Based on runs in Table 1.
†Selectivity set to the value obtained experimentally, and conversion assumed to be 90%.
‡Yield calculated based on HMF present in the organic stream sent to the evaporator.

EXAMPLES

The following Examples are included solely to afford a more complete understanding of the process disclosed and claimed herein. The Examples do not limit the scope of the invention in any fashion.

The following series of Examples were performed to identify key processing variables for HMF and furfural production using the modified biphasic system described hereinabove. The overarching goal of the Examples was to improve the selectivity of the reaction when using less-reactive molecules as reactants, such as glucose, xylose, sucrose (a disaccharide of glucose and fructose), inulin (a polyfructan), starch (a polyglucan with α-1,4 glycoside linkages), cellobiose (a glucose dimer with β-1,4 glycoside linkages) and xylan (a polysaccharide with xylose monomer unit). These reactants are desirable because they are inexpensive and abundantly available. By directly processing these highly functionalized polysaccharides, the need to obtain simple carbohydrate molecules by acid hydrolysis as a separate processing step is eliminated. In short, the reaction can proceed directly, in the absence of an initial hydrolysis reaction of the raw carbohydrate feedstock.

Standard Operating Procedures for the Examples

Aqueous- and organic-phase components including carbohydrates (fructose, glucose, sucrose, etc.) DMSO, PVP (average M. W. 10,000), MIBK, 2-butanol, HCl, $H_2SO_4$ and $H_3PO_4$ were obtained from Sigma-Aldrich Corp (St. Louis, Mo.). These reagents are also available from a large number of other national and international commercial suppliers. The ion-exchange resin, PK-216, was obtained from Mitsubishi Chemicals and was activated by mixing it with 5 bed volumes of 2 M HCl for 30 min, followed by extensive washing with de-ionized (DI) water and subsequent drying for 10 h at 343 K.

Batch catalytic experiments were carried out in 10 ml (Alltech), thick-walled glass reactors heated in a temperature controlled oil bath placed on top of a magnetic stirrer. The temperature in the oil bath was measured by a K-type thermocouple (Omega Engineering, Inc., Stamford, Conn.) and controlled using a series 16A temperature controller (Dwyer Instruments, Michigan City, Ind.) coupled with a 150 W heating cartridge (McMaster-Carr, Atlanta, Ga.). In a typical high-temperature experiment, 1.5 g of 0.25 M HCl aqueous phase solution and 1.5 g of organic phase solution were poured into the reactor (Runs 40-41 and 42-43 in Table 1 (above) used 0.5 M $H_2SO_4$ and 0.75 M $H_3PO_4$, respectively). The reaction was carried out in an oil bath set at reaction temperature and for the reaction times as indicated in Table 1 and 3. The reaction was stopped by rapidly cooling the reactor in an ethylene glycol bath set at 253 K. In a typical low-temperature experiment, 5 g of aqueous phase solution, 5 g of organic phase solution and ion exchange resin in a 1:1 w/w fructose:resin ratio were poured into a 25 ml glass reactor (Alltech). The reactor was then placed in an oil bath set at 353 K for 8-16 h to obtain fructose conversions close to 75%. In a typical run carried out with DCM, 7 g of aqueous phase solution and 7 g of DCM were filled in 23 ml Parr reactors with no catalyst added. Runs were carried out for 1-12 h of reaction times as indicated in Table 3.

After reaction, the reactors were cooled and the aqueous and organic phases were sampled and analyzed using HPLC. Sample analyses were performed by HPLC using a Waters 2690 system equipped with PDA 960 UV (320 nm) and RI-410 refractive index detectors. Fructose disappearance was monitored with an Aminex-brand HPX-87H column (Biorad, Hercules, Calif.), using MilliQ water (pH=2) as the mobile phase at a flow rate of 0.6 ml/min and a column temperature of 303 K. HMF was quantified in the aqueous and organic phases with a Zorbax SB-C18 reverse phase column (Agilent, Palo Alto, Calif.), using a 2:8 v/v Methanol: Water (pH=2) gradient at a flow rate of 0.7 ml/min and a column temperature of 303 K.

The experimental protocol for the Shimadzu GC/MS (GC-17A, QP-5000) with Restek RTX-5 crossbond 5% diphenyl, 95% dimethyl, polysiloxane was as follows: An initial oven temperature of 323 K was held for 3 minutes; next, temperature was ramped at 20 K/min until 598 K was reached. Column pressure started at 100 kPa, held for 3 minutes, ramped at 1 kPa/min until 113 kPa was reached, and then held at 113 kPa for 0.75 minutes. Column flow was 1.7 ml/min.

The experimental protocol for HPLC with the Agilent Zorbax SB-C18 Column was as follows: Column temperature was set at 308 K and flow rate at 0.7 ml/min. Gradient Used: 0-2 min., 100% water pH=2; 2-3 min transition and hold from 3-10 min with 80% water, 20% methanol; 10-11 min mark transition and hold from 11-15 min mark with 20% water, 80% methanol; 15-16 min mark transition and hold until 35 min mark with 100% water.

To characterize the various compounds, mass spectroscopy was performed starting at 33 m/z. The mass spectra and the retention times matched those of commercially available compounds and literature values from the SDBS database run by the National Metrology Institute of Japan. Although mass spectroscopy data for 4 were not available, the mass spectrum of the target compound matched that of the purchased version. For all the compounds described below, the retention times for the GC and the HPLC, as well as the UV signature in the HPLC (when available) matched those of the corresponding purchased compounds. The following compound numbers correspond to those presented in FIG. 1B:

Compound 1: 2,5-dimethylfuran (CAS # 625-86-5), UV/vis: $\lambda_{max}$ 221.5 nm; {Actual MW 96.13} M.S.: m/z (% of max intensity) 39 (14), 41 (12), 43 (100), 51 (11), 53 (41), 67 (5), 81 (16), 95 (34), 96 (37), 97 (3). Retention time in GC/MS is 2.17 min and 19.3 min in HPLC using the methods noted herein.

Compound 3: 5-hydroxymethylfurfural (CAS # 67-47-0), UV/vis: $\lambda_{max}$ 226.2 & 282.8 nm; {Actual MW 126.11} M.S.: m/z (% of max intensity) 37 (10), 38 (18), 39 (56), 41 (100), 51 (12), 53 (14), 81 (3), 97 (43), 109 (4), 125 (4), 126 (22), 127 (2). Retention time in GC/MS is 8.5 min and 10.1 min in HPLC.

Compound 4: 2,5-dihydroxymethylfuran (CAS # 1883-75-6), UV/vis: $\lambda_{max}$ 221.5 nm; {Actual MW 128.13} M.S.: m/z (% of max intensity) 38 (14), 39 (68), 41 (100), 42 (12), 43 (14), 50 (12), 51 (18), 52 (13), 53 (27), 55 (28), 65 (11), 69 (39), 97 (81), 109 (11), 111 (10), 128 (35), 129 (2). Retention time in GC/MS is 8.46 min and 9.7 min in HPLC.

Compound 5: 2-methyl,5-hydroxymethylfuran (CAS # 3857-25-8), UV/vis: $\lambda_{max}$ 221.5 nm; {Actual MW 112.13} M.S.: m/z (% of max intensity) 39 (35), 41 (62), 43 (100), 50 (15), 51 (20), 52 (12), 53 (24), 55 (33), 67 (6), 69 (22), 84 (9), 95 (42), 97 (21), 111 (14), 112 (38), 113 (3). Retention time in GC/MS is 5.75 min and 16.0 min in HPLC.

Compound 6: 2-methylfuran (CAS # 534-22-5), UV/vis: $\lambda_{max}$ 216.8 nm; {Actual MW 82.10} M.S.: m/z (% of max intensity) 38 (15), 39 (100), 41 (11), 43 (18), 50 (16), 51 (18), 53 (79), 54 (13), 81 (47), 82 (72), 83 (4). Retention time in GC/MS is 1.52 min and 17.8 min in HPLC.

Compound 7: furfural alcohol (CAS # 98-00-0), UV/vis: $\lambda_{max}$ 216.8 nm; {Actual MW 98.10} M.S.: m/z (% of max intensity) 37 (17), 38 (29), 39 (83), 41 (100), 42 (70), 43 (15), 50 (12), 51 (15), 52 (12), 53 (41), 55 (12), 69 (23), 70 (16), 81 (26), 97 (21), 98 (35), 99 (2). GC/MS ret. time 4.50 min. Retention time in GC/MS is 4.50 min and 11.7 min in HPLC.

Compound 9: 2,5-dimethyltetrahydrofuran (CAS # 1003-38-9), {Actual MW 100.16} M.S.: m/z (% of max intensity) 39 (25), 41(100), 43 (74), 55 (14), 56 (55), 57 (12), 67(10), 85 (27), 100(1), 101 (0.1). GC/MS retention time 2.20 min.

1-Chlorobutane (CAS # 109-69-3): {Actual MW 92.57} M.S.: m/z (% of max intensity) 40 (9), 41 (100), 42 (11), 43 (42), 51 (2), 56 (73), 57 (4), 63 (3), 65 (0.7), 73 (0.3), 75 (0.3). GC/MS retention time 1.73 min.

Fructose conversion and HMF selectivity were calculated from the product of the aqueous and organic phase concentrations obtained in the HPLC and their corresponding measured volumes after reaction. Because the value of $V_{org}/V_{aq}$ changes after reaction, final volumes for each run had to be determined individually by measuring the weight and the density of each phase.

See the various Tables for a complete tabulation of the data discussed in the Examples.

Example 1

Dehydration of Glucose

Keto-hexoses produce higher yields of HMF compared to aldo-hexoses. Thus, most of the reported work described hereinabove focuses on fructose dehydration instead of glucose dehydration. Glucose, however, is more abundant and cheaper than fructose. This Example demonstrates that by optimizing the acid concentration and DMSO content in the reactive aqueous phase, glucose can be converted to HMF or furfural with improved selectivity (defined as moles of HMF or furfural produced divided by moles of carbohydrate consumed). This Example is significant because of the abundance of glucose in commercial markets. The ability to use glucose as a feedstock makes the present invention more attractive to large-scale commercialization.

Figure 6:
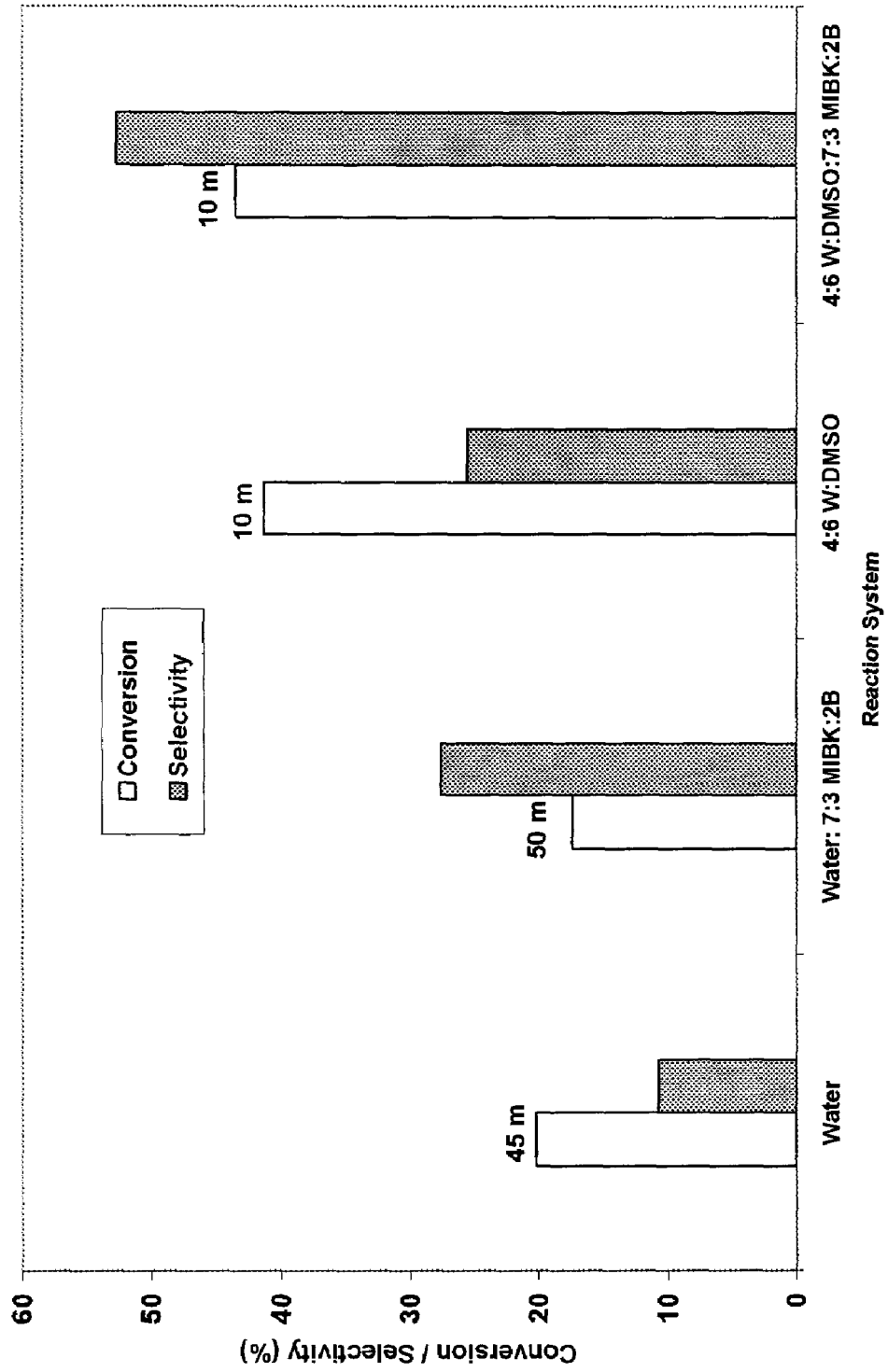
FIG. 6 is a graph depicting the effect of adding aqueous modifiers to the aqueous phase (4:6 water:DMSO) (w/w) and the extracting organic phase (7:3 MIBK:2-butanol) (w/w) on the selectivity and conversion rates for 10 wt % glucose dehydration. White bars represent conversion; grey bars represent selectivity.

The experiments with glucose (the least reactive of the monosaccharides tested) were run in a biphasic reactor as depicted in FIG. 5, using HCl (pH 1.0) as the catalyst. The goal was to maximize the selectivity of the reaction for producing HMF and furfural at 443 K under autonomous pressure. The initial two-phase reaction configuration used pure water as the aqueous phase and MIBK as the organic phase. (In effect, this was the "control" reaction.) The results are shown in the far-left set of bars in FIG. 6 (white bars show conversion rate; grey bars show selectivity; time of reaction is provided above each set of bars). FIG. 6 also shows the effect of adding modifiers to the aqueous phase and/or to the organic phase. Thus, the second pair of bars from the left in FIG. 6 depict the conversion and selectivity rates for the same reaction using water as the aqueous phase, but using as the organic phase a 7:3 mixture of MIBK:2-butanol (w/w).

The third set of bars from the left depicts the results of a single-phase reaction using a 4:6 reaction mixture of water:DMSO (w/w). The far right-hand set of bars depicts the results of biphasic reaction using a 4:6 reaction mixture of water:DMSO (w/w) as the aqueous phase and a 7:3 mixture of MIBK:2-butanol (w/w) as the organic phase.

As shown in FIG. 6, in pure water, HMF selectivity from glucose (see also Table 4, entry 1) was very low and the reaction yielded insoluble byproducts. Adding an extracting solvent improves the selectivity by 17%, with an almost equal improvement for dehydration. The presence of an extracting solvent thus not only improves the selectivity (presumably by minimizing degradation reactions arising from extended HMF residence in the reactive aqueous phase) but also achieves efficient recovery by extracting 82% of HMF into the organic layer for subsequent isolation.

Adding DMSO to the aqueous reactive phase (60 wt %) with no extracting solvent resulted in dramatic improvement in rates for glucose dehydration along with concomitant increase of 16% in the selectivity of the reaction. See FIG. 6, third set of bars from the left. Adding DMSO along with an extracting solvent almost doubled the positive effect by improving rates and increasing the selectivity by 42%. A small amount of DMSO (~8.7 wt % as detected by HPLC analysis) was transferred to the organic phase. In real-world industrial practice, the amount of acid added should be kept as low as possible to avoid corrosion effects and loss of HMF by rehydration to levulinic acid. The overall significance of this Example, as shown by FIG. 6, is that adding DMSO to the aqueous phase, and using an efficient extracting phase (MIBK/2-butanol in this Example) not only improves the dehydration rates and selectivity, but also provides a much simpler separation system for product purification.

Example 2

Effect of pH on Dehydration of Fructose, Glucose, and Xylose

Figure 7:
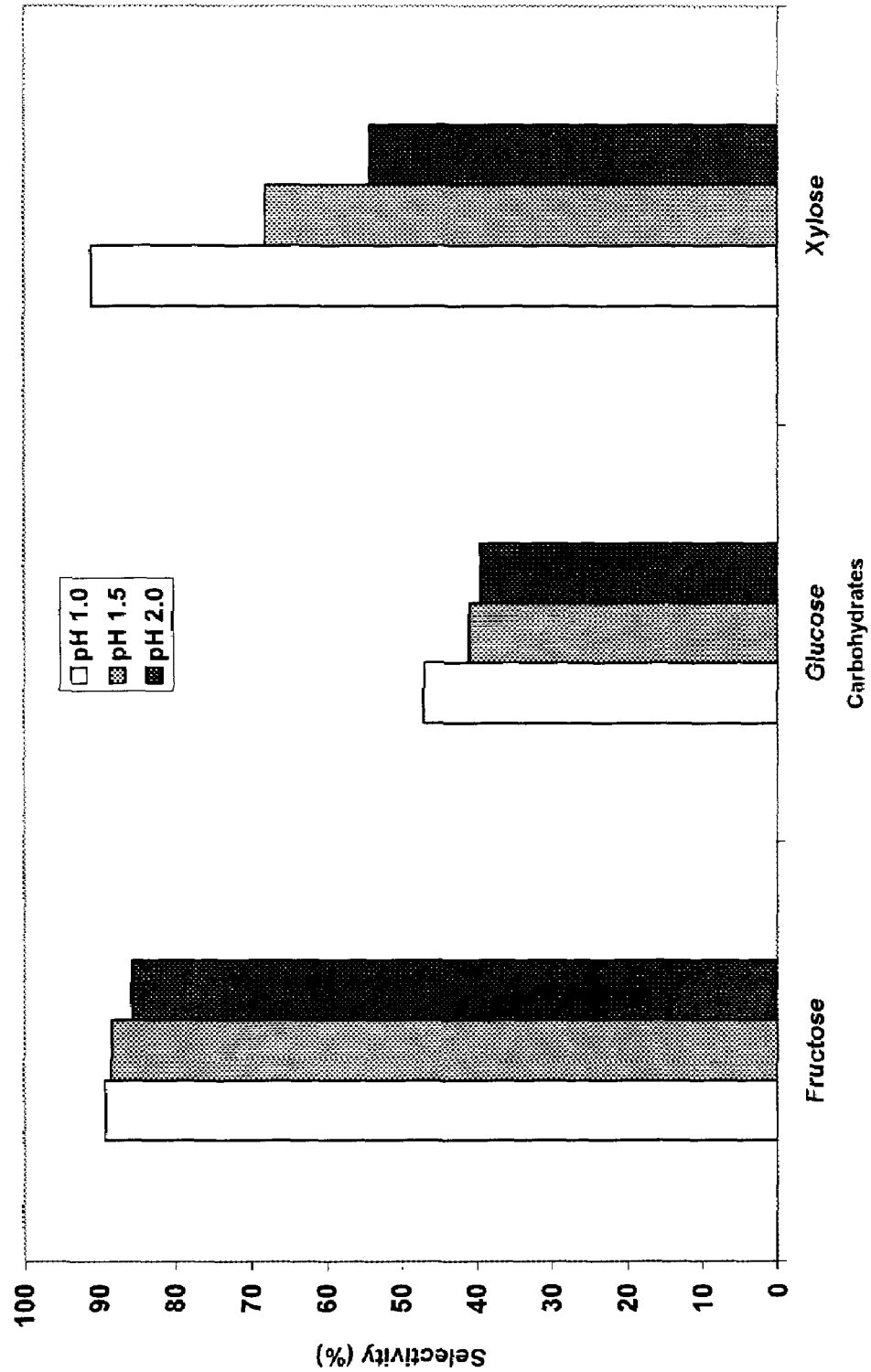
FIG. 7 is a graph depicting the effect of acid concentration on the selectivity (%) for dehydration of 10 wt % solutions of simple sugars fructose, glucose, and xylose. These experiments were conducted in a 5:5 water:DMSO mixture at 443 K using 7:3 MIBK:2-butanol as the extracting solvent. White bars=pH 1.0; light grey bars=pH 1.5; dark grey bars=pH 2.0.

This Example investigated the effects of varying the acid concentration on the dehydration reaction of the simple carbohydrates fructose, glucose, and xylose. These three sugars display a wide difference in their respective reactivities and selectivities toward the desired product. Again, the reactions were run in a biphasic reactor as shown in FIG. 5. The reactions were carried out at various pH's (1.0, 1.5, and 2.0) using an aqueous phase of a 5:5 mixture of water:DMSO (w/w) and an organic phase of a 7:3 mixture of MIBK:2-butanol (w/w), at a temperature of 443 K. The results are shown in FIG. 7 (white bars=pH 1.0; light grey bars=pH 1.5; dark grey bars=pH 2.0).

The reactivity of the processing conditions increases with increasing DMSO content and decreasing pH (i.e., increasing acidity). It can be seen from FIG. 7 that fructose dehydration to HMF had maximum rates for dehydration among the three sugars tested, with selectivities higher than 85%, at high conversion (>90%), at all three levels of acidity. A small increase in both selectivity (about 5%) and rate was observed with a decrease in pH. Similar effects in selectivity and rate were observed for glucose dehydration as HMF selectivity improved by 7% and rate by 400% with a decrease in pH from 2.0 to 1.0. (See the middle set of bars in FIG. 7.) These results clearly indicate the inherent difference in dehydration rates and selectivities of keto-hexoses and aldo-hexoses in similar reacting environments. For xylose dehydration to furfural, a significant rise in the selectivity of up to about 91% (pH 1.0) from 54% (pH 2.0) was observed, along with a 6-fold improvement in dehydration rates when moving from pH 2.0 to pH 1.0. See the right-hand set of bars in FIG. 7.

Example 3

Effect of DMSO Concentration on Glucose Dehydration

In this Example, the effect of DMSO concentration on the dehydration of glucose was investigated. Here, the reactions were carried out at a constant pH (1.0), at 443 K. The aqueous phase reaction solution was then varied (pure water, a 5:5 mixture of water:DMSO (w/w), or a 4:6 mixture of water:DMSO). In each reaction, a 7:3 mixture of MIBK:2-butanol (w/w) was used as the organic phase. The combined results for conversion (white bars), selectivity (grey bars), and the ratio of the product in the aqueous phase vs the organic phase (R, solid line) are shown in FIG. 8.

Figure 8:
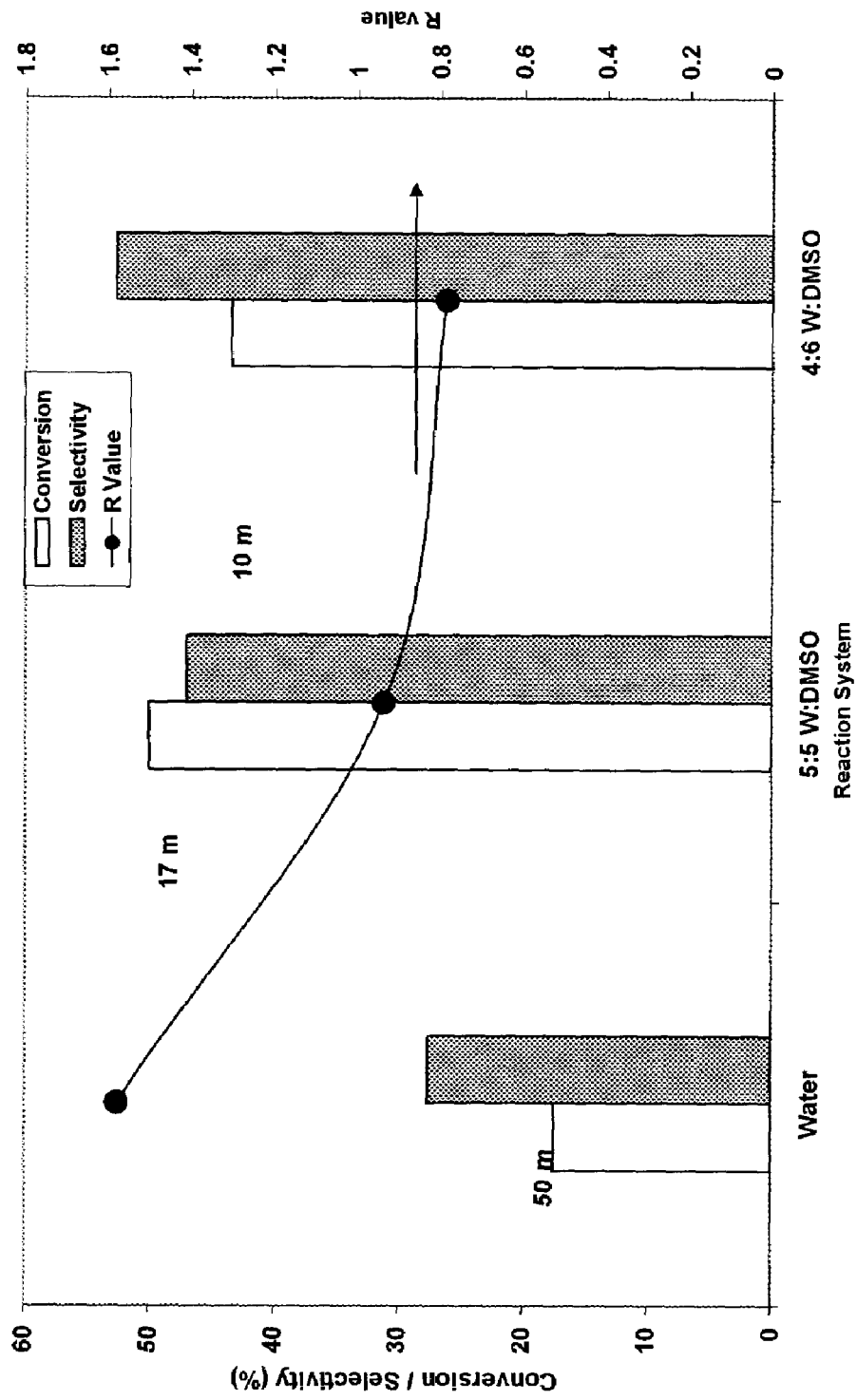
FIG. 8 is a graph depicting the effects of varying the DMSO concentration on 10 wt % glucose dehydration at a constant pH of 1.0, at 443 K, using 7:3 MIBK:2-butanol as the extracting solvent.

FIG. 8 shows that increasing the DMSO content to 50 wt % improves the selectivity by about 18%, with a further increase of about 7% for an additional 10 wt % increase in DMSO content. It is important to note that simply increasing the DMSO content by 10 wt % (from 5:5, water:DMSO to 4:6 water:DMSO) doubles the dehydration rates. While not being bound to any underlying physical or chemical phenomenon, it appears that DMSO suppresses both the formation of condensation byproducts and HMF rehydration by lowering the overall water concentration. The effect, however, is not without certain drawbacks: increasing the DMSO content simultaneously decreases the extracting power of the organic phase as indicated by a decrease in value of R. See the solid line in FIG. 8. "R" is defined herein as the ratio of HMF concentration in the organic phase to the HMF concentration in the aqueous phase. As shown in FIG. 8, moving from a pure water aqueous phase to a 4:6 water:DMSO aqueous phase dropped the value of R from 1.58 to 0.8. This signifies that the water-DMSO mixture had a higher affinity for HMF as compared to pure water.

As pointed out in Example 1, a small fraction of DMSO is carried over to the organic phase, which is undesirable for purposes of recovering purified HMF from the organic phase. The potential problem of DMSO contamination in the HMF product can be minimized by decreasing the DMSO content. The carry-over of DMSO from the aqueous phase into the organic phase dropped by 4% as the DMSO fraction was decreased from 60 wt % to 50 wt % (data not shown). Thus, a balance can be struck by optimizing the DMSO concentration in the aqueous phase to maximize HMF selectivity and to minimize DMSO carry-over into the organic phase. In short, as shown by Examples 1, 2, and 3, by increasing the amount of DMSO content and the acidity, selectivity above 50% can be obtained for glucose dehydration to HMF.

Example 4

Dehydration of Other Carbohydrates

In Examples 1, 2, and 3, the dehydration of simple carbohydrates was optimized by adjusting the pH and DMSO content to achieve good selectivities and reaction rates. In summary, fructose gives an optimum selectivity of 88% at pH 1.5, while xylose achieves 91% selectivity at pH 1.0 with a 5:5 water:DMSO aqueous reacting phase.

For glucose, the least reactive of the monosaccharides tested, increased DMSO levels (up to 60%) and acidity (pH 1.0) is required to achieve a best selectivity of 53%.

Figure 9:
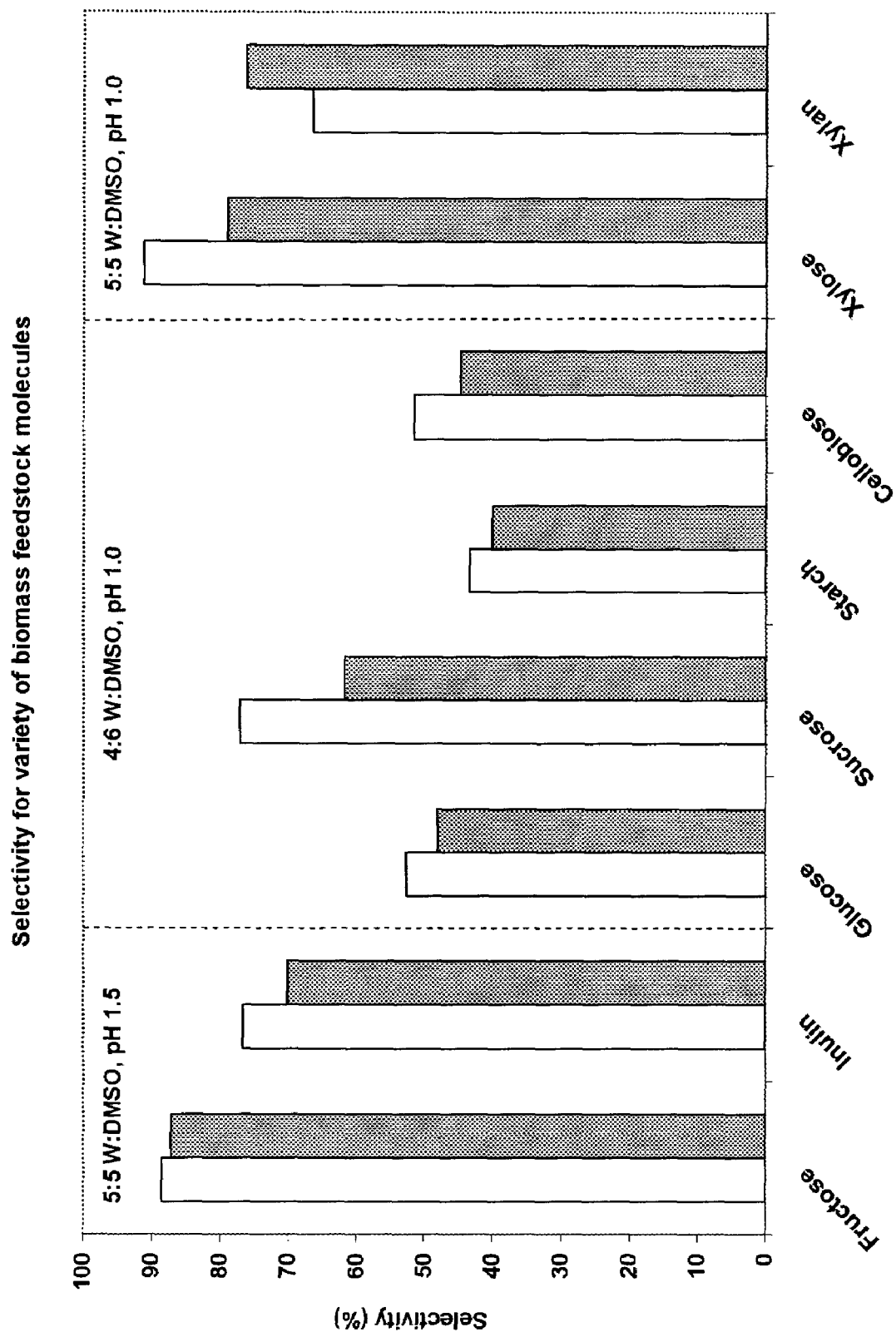
FIG. 9 is a graph depicting the effect on selectivity of subjecting a variety of carbohydrate precursor molecules with 10 wt % initial concentrations at optimized conditions for their monomer units. White bars present a water:DMSO aqueous reaction mix using HCl as the catalyst; grey bars represent using 3:7 water:DMSO-5 DCM.

FIG. 9 presents the corresponding effects of subjecting a variety of carbohydrate precursor molecules at optimized conditions for their respective monomer units. FIG. 9 presents three groups of data for the precursor and the corresponding monomers: (1) inulin and fructose; (2) sucrose, starch, cellobiose and glucose; and (3) xylan and xylose. The white bars present the data for reactions conducted in 5:5 water:DMSO aqueous phase and a 7:3 MIBK:2-butanol organic phase. The grey bars present the data for reactions conducted in a 3:7 (w/w) mixture of water:DMSO, but using dichloromethane as the organic phase.

Subjecting inulin, a fructose precursor molecule obtained from chicory, to dehydration in 5:5 water:DMSO at pH 1.5 gives a selectivity of 77% at high conversion. These values compare favorably (and consistently) with the results for fructose (assuming some loss due to hydrolysis of the polysaccharide to fructose). See the left-hand portion of FIG. 9.

Similarly subjecting sucrose (a disaccharide consisting of a fructose residue and a glucose residue) to dehydration in an aqueous phase of 4:6, water:DMSO at pH 1.0 achieves 77% selectivity at 65% sucrose conversion. See the middle section of FIG. 9. At these processing conditions, fructose would be completely converted to HMF. Assuming a glucose conversion of about 30% (a safe assumption based on the data shown in the earlier Examples) the expected selectivity for sucrose is about 81%. Thus, the reaction of sucrose according to the present invention closely follows the selectivity trends set by its monomer units (i.e. fructose at 90% selectivity and glucose at 53% selectivity).

Cellobiose, a glucose dimer connected by β-1,4 glycoside linkages gave a similar selectivity (52%) as that of the glucose monomer unit.

Soluble starch also gave similar results. Soluble starch (which is a precursor for the glucose monomer) is linked by α-1,4 glycoside linkages and is readily obtained from corn, rice, etc. It is a commodity product. When processed at these same conditions, soluble starch yielded a selectivity for HMF of 43%.

Xylan is used in this Example as a representative polymer for hemi-cellulose. Xylan contains the monomer xylose. When subjected to dehydration in a 5:5 water:DMSO reaction solution, at pH 1.0, xylan gave a selectivity of 66% at high conversions. See the right-hand portion of FIG. 9. Thus, by optimizing the processing conditions for simple sugars, a variety of biomass feedstocks (which contain more complex carbohydrates, and which are inexpensive and abundantly available) can be processed with equivalent yields for furan derivates via the dehydration reaction disclosed herein.

Quite remarkably (and wholly unexpectedly), DCM is able to process all of the carbohydrate feed molecules described above at a temperature of 413 K with no acid catalyst at all. As seen in FIG. 9 (grey bars), all the feedstock molecules matched up well in selectivity at high conversions using a 3:7 mixture of water:DMSO as reactive aqueous phase (without any acid present) and an equal amount of DCM as the extracting organic phase. The unexpected ability of this solvent combination to process a variety of biomass feed molecules with good selectivity and no catalyst required is extremely beneficial because it solves the corrosion problems inherent when conducting reacts at or below pH 2 using mineral acids. By eliminating the harsh acidic environment, the reactions can be carried out without encountering the corrosions problems inherent in low pH environments.

Additionally, the extracting power of the organic phase is higher for DCM (R=1.35) as compared to mixture of 7:3 MIBK:2-butanol (R=0.8). However, this advantage is offset, at least in part, by the significantly increased carry-over of DMSO into the DCM (up to 20 wt %) thereby increasing the subsequent cost of recovering the product.

It has been shown that DCM can undergo hydrolysis in presence water at high temperature (about 250° C.) to generate aqueous HCl (citation omitted). To investigate this phenomenon in the context of the present invention, water and DCM were subjected to 413 K for 3 h. A drop in pH to about 2.0 was noted. Subsequent GC-MS analysis of the aqueous phase showed the presence of a trace amount of HCl. A similar experiment with 3:7 water:DMSO-5 DCM with no sugar feed resulted in the pH dropping to about 1.5, but no trace of HCl was found. This could possibly be because the high fraction of DMSO is associated with water and hence water is not available for the DCM hydrolysis to HCl to take place. However, small traces of decomposition products from DMSO were noticed in GC-MS; these decomposition products may impart acidity to the solvent mixture. Nevertheless, the reaction process using DCM as the organic phase is highly useful because it can process insoluble solid biomass feedstocks, along with soluble carbohydrate moieties, and yield high concentrations of substituted furan compounds (all without requiring an added acid catalyst).

Example 5

Using Different Acids as Catalyst

Along with HCl, experiments were conducted with $H_2SO_4$ and $H_3PO_4$ at a controlled pH 1.5. The aqueous reaction phase was a 5:5 mixture of water:DMSO (w/w) and the organic phase was a 7:3 mixture of MIBK:2-butanol (w/w). Glucose was used as the reactant. The results are presented in FIG. 10, where the white bars represent conversion and the grey bars represent selectivity.

Figure 10:
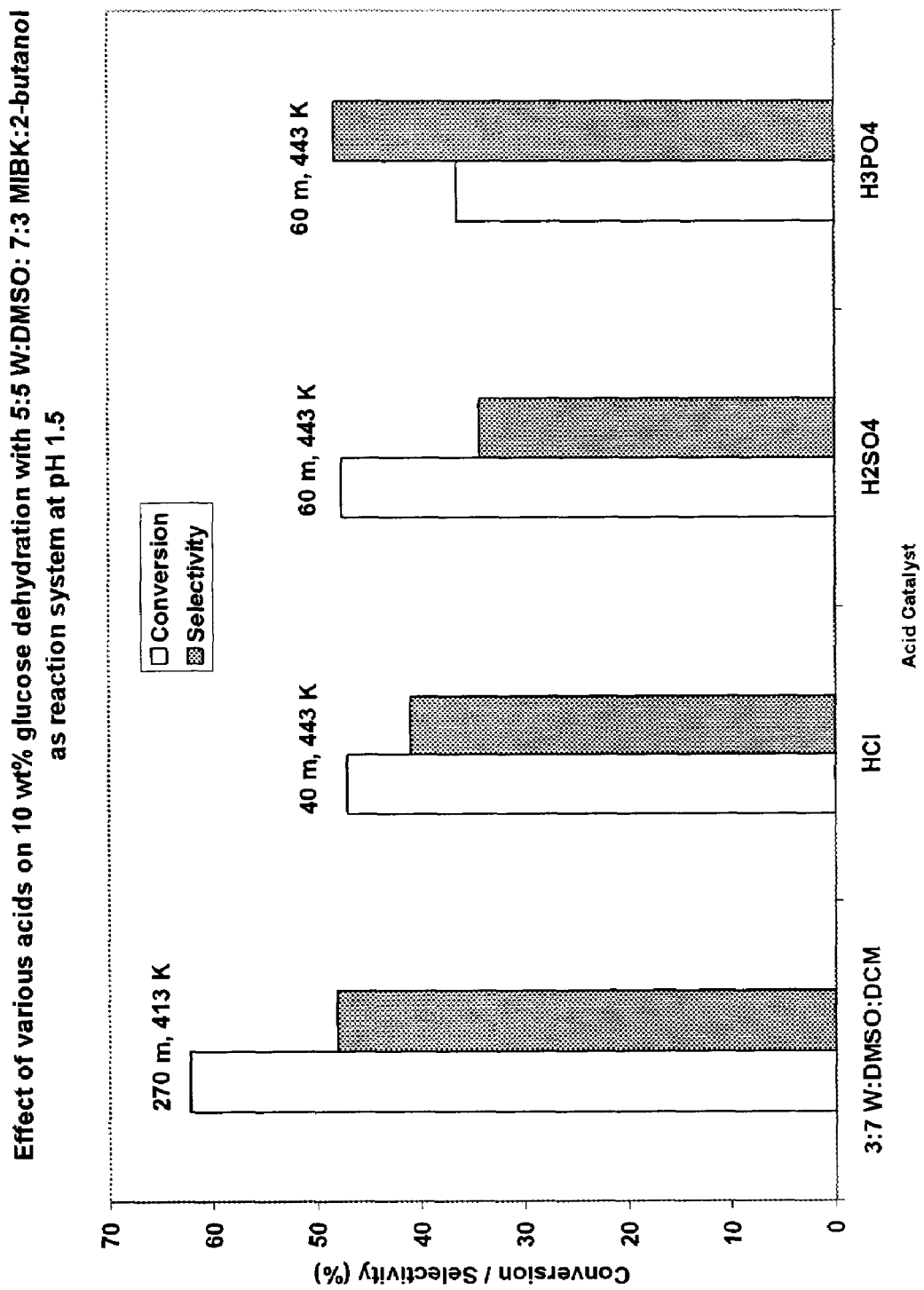
FIG. 10 is a graph depicting the effect of using different mineral acids as the catalyst on 10 wt % glucose dehydration.

As seen from FIG. 10, all of the acids tested showed different selectivities, with $H_3PO_4$ achieving a selectivity essentially identical to the selectivity of the 3:7 water:DMSO-DCM system. Sulphuric acid showed the least selectivity (34%) and HCl had a selectivity of 41%. It is important to note that even though the acidity level (pH 1.5) was constant for all of the systems run in this example, the systems yielded different results for HMF selectivity. In short, at least in this brief Example, the results using the 3:7 DMSO-DCM system could not be emulated by replacing the 3:7 DMSO-DCM with a mineral acid and using MBIK:2-butanol.

Example 6

Adding Salts to the Aqueous Layer

The results from the above Examples show that, for a specific aqueous phase composition, the selectivity for producing HMF can be increased by increasing the value of the extracting ratio, R. This leads to more effective partitioning of the HMF into the organic layer and out of the reactive aqueous layer. Moving more of the HMF into the organic layer thus minimizes undesirable side-reactions of HMF within the aqueous layer. This Example shows that the extracting ratio R can be increased by adding a salt such as NaCl to the aqueous phase.

A first reaction was run at 180° C., with 30 wt % fructose in water, and using 7:3 MIBK:2-butanol as the extracting solvent. This reaction yielded an R value of 1.65. The selectivity for HMF production was equal to 70% at 68% conversion, using HCl as the catalyst (0.25 M), and using a volume of extracting solvent equal to 1.56 times the volume of the aqueous layer.

A second reaction using 30 wt % fructose in water saturated with NaCl, and all other variable identical to the first reaction, yielded an R value of 3.75, more than twice the value obtained without NaCl. HMF selectivity for the second reaction was 77% at 80% conversion. The presence of the metal salt thus enhances the partitioning of HMF into the organic phase by lowering the solubility of HMF in the aqueous phase, which in turn decreases HMF degradation in the aqueous medium.

Example 7

Adding Multiple Salts to the Aqueous Layer

The results from Example 6 show that the addition of a salt to the aqueous layer improves the partitioning of HMF into organic phase by lowering the solubility of HMF in the aqueous phase and thus improves HMF selectivity. Adding more than one salt to the aqueous layer can increase further the value of R. This Example shows that the extraction ratio R is further increased by adding a combination of salts such as NaCl and $NaSO_4$ to the aqueous phase.

A first reaction was run at 180° C., with 30 wt % fructose in water saturated with NaCl, and using 1-butanol as the extracting solvent. This reaction yielded an R value of 2.97. The selectivity for HMF production was equal to 81% at 80% conversion, using HCl as the catalyst (0.25 M), and using a volume of extracting solvent equal to 3.2 times the volume of the aqueous layer.

A second reaction using 30 wt % fructose in water saturated with both NaCl and $NaSO_4$, and all other variable identical to the first reaction, yielded an R value of 4.0. HMF selectivity for the second reaction was 85% at 80% conversion. The presence of both metal salt thus enhances the partitioning of HMF into the organic phase even further than just using NaCl.

Example 8

Vapor Phase Hydrogenolysis

Catalyst Preparation: CuRu/C catalysts were prepared by incipient wetness impregnation of a commercial catalyst comprising 10 wt % Ru on carbon: C-10: HP ruthenium on Vulcan XC-72 (E-TEK Division, PEMEAS Fuel Cell Technologies, purchased by BASF in February 2007 and re-named BASF Fuel Cell, Somerset, N.J.) with a copper nitrate ($CuNO_3*2.5H_2O$, Sigma-Aldrich) water solution. For a typical batch of 3:2 (molar ratio) Cu:Ru catalyst, 1.55 g of copper nitrite was dissolved in 5 g of deionized (DI) water. This solution was then added drop-wise to 4.58 g of Ru/C catalyst. Following impregnation, the catalyst was dried in air at 403 K for 2 h and reduced at 523 K in flowing hydrogen for 10 h (0.42 K/min ramp for 6 h followed by 4 h at 523 K). After reduction, the catalyst was allowed to cool to room temperature and passivated in flowing 2% oxygen in helium for 3 h. All gas flow rates were maintained at approximately 110 $cm^3$(STP)/min. Pre-reduced, barium-promoted $CuCrO_4$ was used untreated from Sigma-Aldrich.

Batch Reactor System: All batch reactor runs were carried out using an autoclave reactor with external temperature and stirring controller (Model 4566 and 4836, Parr Instrument Co.). For a typical hydrogenolysis run, 2.5 g of HMF (98%, Sigma-Aldrich) was dissolved in 47.5 g of organic solvent. The solvent was either dry 1-butanol (99.9%, Sigma-Aldrich) or 1-butanol pre-contacted with a NaCl/water solution that simulated the final untreated organic layer from the biphasic fructose dehydration step. The NaCl/water solution was made by adding 6.7 g sodium chloride into 18.9 g deionized water. Next, 51 g of 1-butanol was added to the NaCl/water solution and shaken vigorously. The resulting two phases were allowed to separate for 20 minutes.

TABLE 4

Results for acid catalyzed dehydration of various carbohydrate feedstock's. Runs 1-20, except 14 and 15, were carried out in 10 wt % initial concentration of carbohydrate in presence of HCl as catalyst at 443K. Runs 14 and 15 were carried out in presence of $H_2SO_4$ and $H_3PO_4$ acid as catalyst respectively. Run 1-20 used twice the amount of organic solvent by weight with respect to aqueous phase. Runs 21-28 were carried out with 10 wt % initial concentration of carbohydrate with no catalyst at 413K in presence of equal amount by weight of dichloromethane (DCM) as solvent. Aqueous phase and Organic phase composition are based on w/w ratios. Conversion is defined as ratio of carbohydrate consumed to carbohydrate added initially. Selectivity is defined as ratio of HMF or Furfural produced to carbohydrate consumed. $R = [\text{HMF or Fur}]_{org}/[\text{HMF or Fur}]_{aq}$.

| Run # | Sugar | Aqueous Phase Composition | Organic Phase Composition | pH | Time (h:min) | Conversion (%) | Selectivity (%) | HMF or Fur Organic Phase (%) | [HMF or Fur]$_{org}$ [g/cc] | [HMF or Fur]$_{aq}$ [g/cc] | R |
|---|---|---|---|---|---|---|---|---|---|---|---|
| 1 | Glucose | Water | — | 1.0 | 0:45 | 20 | 11 | 0 | 0 | 0.00152 | 0.00 |
| 2 | Glucose | Water | 7:3 MIBK:2-butanol | 1.0 | 0:50 | 17 | 28 | 82 | 0.00103 | 0.00065 | 1.58 |
| 3 | Glucose | 4:6 W:DMSO | — | 1.0 | 0:10 | 41 | 26 | 0 | 0 | 0.00826 | 0.00 |
| 4 | Glucose | 4:6 W:DMSO | 7:3 MIBK:2-butanol | 1.0 | 0 | 43 | 53 | 74 | 0.00434 | 0.00554 | 0.78 |
| 5 | Fructose | 5:5 W:DMSO | 7:3 MIBK:2-butanol | 1.0 | 0:04 | 95 | 89 | 74 | 0.01668 | 0.01901 | 0.88 |
| 6 | Fructose | 5:5 W:DMSO | 7:3 MIBK:2-butanol | 1.5 | 0:06 | 94 | 88 | 76 | 0.01625 | 0.01803 | 0.90 |
| 7 | Fructose | 5:5 W:DMSO | 7:3 MIBK:2-butanol | 2.0 | 0:08 | 95 | 86 | 77 | 0.01616 | 0.01686 | 0.96 |
| 8 | Glucose | 5:5 W:DMSO | 7:3 MIBK:2-butanol | 1.0 | 0:17 | 50 | 47 | 76 | 0.00471 | 0.00504 | 0.94 |
| 9 | Glucose | 5:5 W:DMSO | 7:3 MIBK:2-butanol | 1.5 | 0:42 | 47 | 41 | 76 | 0.00378 | 0.00419 | 0.90 |
| 10 | Glucose | 5:5 W:DMSO | 7:3 MIBK:2-butanol | 2.0 | 1:40 | 48 | 40 | 76 | 0.00367 | 0.00417 | 0.88 |
| 11 | Xylose | 5:5 W:DMSO | 7:3 MIBK:2-butanol | 1.0 | 0:12 | 71 | 91 | 91 | 0.01414 | 0.00474 | 2.98 |
| 12 | Xylose | 5:5 W:DMSO | 7:3 MIBK:2-butanol | 1.5 | 0:27 | 82 | 68 | 92 | 0.01205 | 0.00360 | 3.35 |
| 13 | Xylose | 5:5 W:DMSO | 7:3 MIBK:2-butanol | 2.0 | 0:55 | 53 | 54 | 92 | 0.00618 | 0.00198 | 3.12 |
| 14 | Glucose | 5:5 W:DMSO | 7:3 MIBK:2-butanol | 1.5 | 1:00 | 48 | 34 | 77 | 0.00322 | 0.00354 | 0.91 |
| 15 | Glucose | 5:5 W:DMSO | 7:3 MIBK:2-butanol | 1.5 | 1:00 | 36 | 48 | 75 | 0.00350 | 0.00369 | 0.95 |
| 16 | Inulin | 5:5 W:DMSO | 7:3 MIBK:2-butanol | 1.5 | 0:05 | 98 | 77 | 76 | 0.0163 | 0.0180 | 0.90 |
| 17 | Sucrose | 4:6 W:DMSO | 7:3 MIBK:2-butanol | 1.0 | 0:05 | 65 | 77 | 75 | 0.0101 | 0.0124 | 0.82 |
| 18 | Starch | 4:6 W:DMSO | 7:3 MIBK:2-butanol | 1.0 | 0:11 | 61 | 43 | 74 | 0.0055 | 0.0069 | 0.79 |
| 19 | Cellobiose | 4:6 W:DMSO | 7:3 MIBK:2-butanol | 1.0 | 0:10 | 52 | 52 | 74 | 0.0056 | 0.0070 | 0.79 |
| 20 | Xylan | 5:5 W:DMSO | 7:3 MIBK:2-butanol | 1.0 | 0:25 | 100 | 66 | 91 | 0.0123 | 0.0041 | 2.98 |
| 21 | Fructose | 3:7 W:DMSO | DCM | — | 2:00 | 100 | 87 | 61 | 0.0384 | 0.0315 | 1.22 |
| 22 | Inulin | 3:7 W:DMSO | DCM | — | 2:30 | 100 | 70 | 62 | 0.0344 | 0.0274 | 1.26 |
| 23 | Glucose | 3:7 W:DMSO | DCM | — | 4:30 | 62 | 48 | 63 | 0.0136 | 0.0100 | 1.36 |
| 24 | Sucrose | 3:7 W:DMSO | DCM | — | 4:30 | 82 | 62 | 64 | 0.0245 | 0.0176 | 1.39 |
| 25 | Starch | 3:7 W:DMSO | DCM | — | 11:00 | 91 | 40 | 65 | 0.0189 | 0.0129 | 1.47 |
| 26 | Cellobiose | 3:7 W:DMSO | DCM | — | 9:30 | 85 | 45 | 68 | 0.0206 | 0.0125 | 1.64 |
| 27 | Xylose | 3:7 W:DMSO | DCM | — | 3:00 | 72 | 79 | 87 | 0.0327 | 0.0063 | 5.2 |
| 28 | Xylan | 3:7 W:DMSO | DCM | — | 3:00 | 100 | 76 | 85 | 0.0362 | 0.0084 | 4.3 |

Afterwards the organic layer was siphoned off and used as the solvent. Next, 0.75 g of CuRu/C catalyst was added to the reactor. The reactor was sealed and purged of air by adding and releasing hydrogen to a pressure of 20 bar. Hydrogenolysis reactions were carried out at 493 K with 6.8 bar initial hydrogen pressure for 10 h while using a stirring speed of 400 rpm. These conditions were found to be optimal for DMF yield. After 10 h the reactor was cooled to room temperature before its contents were sampled, filtered (using 0.2 μm PES syringe membrane filter), and analyzed.

Flow Reactor: A down-flow, vapor-phase, fixed-bed reactor setup was used to convert HMF to DMF. One gram of catalyst in powder form was mixed with 2.3 g of silicon dioxide fused granules with a 4 to 16 mesh size (Aldrich) and loaded into a ¼" outside diameter tubular stainless steel reactor. The catalyst bed was contained in the tubular reactor by an end-plug of quartz wool (Alltech). A Type-K thermocouple (Omega) attached to the outside of the reactor was used to measure the reactor temperature, which was controlled with a 16A series temperature controller (Dwyer Instruments). The flow rate of $H_2$ was controlled with a mass-flow meter (5850 Brooks Instruments). An HPLC pump (Model 301, Alltech) was used to introduce the feed solution into the down-flow reactor through a needle. The effluent from the reactor was condensed at room temperature in a separator, allowing for periodic sampling of the liquid product stream. The effluent gas stream passed through a back-pressure regulator (GO Regulator, Model BP-60) which controlled the system pressure and through a flowmeter to measure the gas flow rate.

All runs were carried out at 100% conversion at a temperature of 493 K, using a liquid feed rate of 0.2 cm³/min, and a weight hourly space velocity (defined as $g_{HMF}/(h\, g_{catalyst})$ of 0.147 h$^{-1}$ and of 0.98 h$^{-1}$ for 1.5 and 10 wt % runs. Other process conditions used in the experiments are listed in Table 6. Product sampling took place approximately every 3 to 6 cm³ of liquid feed, and reported values are mean values over all steady state points.

Detailed results for the vapor phase hydrogenolysis reactions performed under a variety of conditions and using various metal catalysts are presented in Tables 5, 6, and 7. Referring to Table 7, no signs of deactivation for feeds consisting of 1.5 wt % HMF were observed. Runs 6-9 used the same 1 g of CuRu/C catalyst, which underwent overnight reductions at 493 K in flowing H$_2$ at 40 cm³(STP)/min. Signs of catalyst deactivation were observed when 10 wt % HMF feeds were used. Deactivation was observed after processing an amount of HMF corresponding to about 1.7 times the catalyst mass. Notably, however, it was found that after deactivation became apparent, treatment for 2 h at 493 K in flowing hydrogen at 40 cm³ (STP)/min was sufficient to regenerate the catalyst to initial performance, as shown by Runs 10-12, which showed 76 to 79% DMF yield.

Specifically, after deactivation of the catalyst observed in Run 10, the aforementioned regeneration step was employed, followed by data collection in Run 11; after catalyst deactivation in Run 11, the catalyst was regenerated by treatment for 2 h at 573 K in flowing H$_2$ at 150 cm³ (STP)/min H$_2$, followed by data collection in Run 12. Run 14[†], unlike all other runs which used purchased HMF, was an integrated run where the HMF was produced in the biphasic reactor and the 1-butanol layer was roto-evaporated, neutralized, and diluted (for comparison to the control Run 13) before being fed to the CuRu/C catalyst. In Run 15, DMF was used as the feed to the reactor, showing that approximately 7% of it remains on the catalyst. This buildup of carbon eventually leads to catalyst deactivation, such that the DMF yield starts to decrease and the yields of intermediates 4 and 5 increase. As can be seen by the carbon out/in column, approximately 80% of the carbon is recovered in a typical run.

TABLE 5

Fructose Dehydration Using Other Inorganic Salts

| Aqueous Phase | Salt | Organic phase | Conversion (%) | Selectivity HMF (%) | R |
|---|---|---|---|---|---|
| 30 wt % fructose | NaBr | 2-butanol | 83 | 78 | 2.0 |
| | KCl | | 89 | 82 | 2.6 |
| | KBr | | 86 | 76 | 1.7 |
| | CaCl$_2$ | | 70 | 78 | 2.7 |
| | CsCl | | 72 | 76 | 2.0 |
| | MgCl$_2$ | | 78 | 77 | 2.8 |
| | NaNO$_3$ | | LOW REACTIVITY AND | | |
| | Na$_2$SO$_4$ | | SOLID FORMATION | | |
| | Na$_2$HPO$_4$ | | | | |

All dehydration reactions using the salts in the table above were carried out under the same conditions as the experiments reported in Table 1 using salt-saturated aqueous phases and an initial $V_{org}/V_{aq}=3.2$.

TABLE 6

Batch Reactor Liquid Phase Hydrogenolysis

| Run | Catalyst | Pre-contacted with H$_2$O and NaCl | Solvent | Conversion (%) | Selectivity DMF (%) | 5 (%) | 6 (%) | 7 (%) | 8 (%) | Carbon Out/In (%) |
|---|---|---|---|---|---|---|---|---|---|---|
| 1 | 3:1 CuRuC | Yes | 1-butanol | 100 | 41.0 | 8.0 | 5.9 | 22 | 3.3 | 80 |
| 1[†] | 3:1 CuRuC | Yes, and purified | 1-butanol | 100 | 61.0 | 9.4 | 3.6 | 11 | 1.8 | 86 |
| 2 | 3:1 CuRuC | No | 1-butanol | 100 | 71.0 | 5.1 | 4.3 | 7.2 | 1.8 | 89 |
| 3 | CuCrO (Barium promoted) | Yes | 1-butanol | 18 | 0.0 | 0.0 | 0.0 | 0.0 | 0.0 | 82 |
| 3[†] | CuCrO (Barium promoted) | Yes, and purified | 1-butanol | 94 | 6.0 | 12.0 | 2.1 | 2.3 | 0.4 | 87 |
| 4 | CuCrO (Barium promoted) | No | 1-butanol | 100 | 61.0 | 29.0 | 0.0 | 0.0 | 2.8 | 92 |

All runs were carried out at T=493 K, P=6.8 bar $H_2$, stirred at 400 rpm with 5 wt % HMF feed, and sampled at 10 h. In Run 3 and especially 3†, significant amounts of compound 4 were observed and comprise the remainder of the carbon out/in balance. Runs pre-contacted with an aqueous phase saturated with NaCl contain 26 mmol/L of NaCl. †Runs pre-contacted with an aqueous phase saturated with NaCl and then purified by evaporation of 25% of the mass contain 1.6 mmol/L of NaCl.

TABLE 7

Flow Reactor Vapor Phase Hydrogenolysis

| Run | Catalyst | Solvent | Pressure (psi), $H_2$ flow rate (cm³(STP)/min) | Yield HMF (wt %) | DMF (%) | 5 (%) | 6 (%) | Carbon Out/In (%) |
|---|---|---|---|---|---|---|---|---|
| 5 | $CuCrO_4$ | 1-butanol | 250, 19 | 1.5 | 52.0 | 0.0 | 0.0 | 52 |
| 6 | 3:2 CuRu/C | 1-butanol | 250, 19 | 1.5 | 77.0 | 0.0 | 0.0 | 77 |
| 7 | 3:2 CuRu/C | 1-butanol | 50, 19 | 1.5 | 62.0 | 0.0 | 4.0 | 66 |
| 8 | 3:2 CuRu/C | 1-hexanol | 100, 42 | 1.5 | 78.0 | 0.0 | 0.0 | 78 |
| 9 | 3:2 CuRu/C | 1-hexanol | 100, 42 | 10.0 | 78.0 | 4.0 | 2.0 | 84 |
| 10 | 3:2 CuRu/C | 1-butanol | 250, 19 | 10.0 | 76.0 | 0.0 | 2.0 | 78 |
| 11 | 3:2 CuRu/C | 1-butanol | 250, 19 | 10.0 | 79.0 | 6.0 | 1.0 | 86 |
| 12 | 3:2 CuRu/C | 1-butanol | 250, 19 | 10.0 | 76.0 | 5.0 | 1.0 | 82 |
| 13 | 3:1 CuRu/C | 1-butanol | 250, 19 | 1.5 | 72.0 | 0.0 | 0.0 | 72 |
| 14† | 3:1 CuRu/C | 1-butanol | 250, 19 | 1.7 | 72.0 | 0.0 | 0.0 | 72 |
| | | | Dimethylfuran wt (%) | | | | | |
| 15 | 3:2 CuRu/C | 1-butanol | 250, 19 | 1.1 | 93.0 | 0.0 | 0.0 | 93 |

All runs were carried out at T=493 K and 100% conversion of HMF. Data collected at steady state. Runs 6-9, used the same 1 g of CuRu/C catalyst and had overnight reductions at 493 K in flowing $H_2$ at 40 cm³ (STP)/min. Run 11 occurs after Run 10 becomes deactivated and is regenerated through treatment at 493 K for 2 h in flowing $H_2$ at 40 cm³ (STP)/min. Run 12 occurs after Run 11 becomes deactivated and is regenerated at 573 K for 2 h in flowing $H_2$ at 150 cm³ (STP)/min. Runs 13-14\ used the same catalyst. Symbol† indicates an integrated run using HMF produced from dehydration of fructose in which the 1-butanol layer was rotoevaporated, neutralized and diluted (for comparison to the control Run 13) before being fed to the CuRu/C catalyst.

Example 9

Estimation for the Energy Consumption in a Distillation Process for DMF and Ethanol In bioethanol production, a typical stream following sugar fermentation contains ~6 wt % ethanol in water. Cardona and Sanchez calculated that the distillation and dehydration of this stream would require approximately 27.4 MJ/(L of EtOH) to produce fuel-grade ethanol 27. The majority of this energy is associated with phase change of water and ethanol from liquid to vapor. On the same basis, evaporating a stream containing 6 wt % DMF in 1-butanol would require approximately 8.8 MJ/L of DMF. This value represents roughly 33% of the energy required in the ethanol process.

Example 10

Toxicity Research on DMF and DMTHF

Material Safety Data Sheets for DMF from 2006 show that the chemical, physical, and toxicology properties have not been thoroughly tested. Carcinogenic, mutagenic, reproductive, bioaccumulation, mobility, and ecotoxicity data are lacking. The limited information available suggests that DMF is not more toxic than current fuel components. For instance, the lethal DMF dose in rats is 1238 mg/kg body weight (gasoline is ~5000 mg/kg body weight). Also, DMF is a mutagen in hamsters at 8 mmol/L (benzene in gasoline is a mutagen in humans at 1 mmol/L) and is deadly to fathead minnows at 71 mg/L in a 96 hr-LC50 test (aromatic chemicals in gasoline are lethal to fathead minnows at ~2 to 10 mg/L)[28,29].

Long term studies performed at doses similar to those experienced while pumping gasoline or at a refinery (0.01 to 200 ppm, respectively) and long term oral dosages at levels similar to those of gasoline found in ground water will have to be performed before DMF fuel is approved for commercial use 30. Similarly, since no data are available on 9 in regard to being carcinogenic, mutagenic, tetratogenic, a bioaccumulator, its mobility, or ecotoxicity, similar studies should be performed on this compound.

REFERENCES

1. M. Bicker, J. Hirth, H. Vogel, *Green Chemistry* 5, 280 (2003).
2. T. Werpy, G. Petersen, *Top Value Added Chemicals From Biomass* Available electronically at http://www.osti.gov/bridge (2004).
3. K. W. Pentz, Great Britain Published Patent Application No. 2,131,014, published Jun. 13, 1984.
4. G. W. Huber, J. N. Chheda, C. J. Barret, J. A. Dumesic, *Science* 308, 1446 (2005).
5. C. Moreau, M. N. Belgacem, A. Gandini, *Topics in Catalysis* 27, 11 (2004).
6. B. M. F. Kuster, *Starch* 42, 314 (1990).
7. A. Gaset, J. P. Gorrichon, E. Truchot, *Informations Chimie* 212, 179 (1981).
8. J. Lewkowski, *Arkivoc* Available electronically at www.arkat-usa.org/ark/journal/2001/I01_General/403/0113.pdf 17 (2001).
9. Y. Nakamura, S. Morikawa, *Bulletin of the Chemical Society of Japan* 53, 3705 (1980).

10. D. W. Brown, A. J. Floyd, R. G. Kinsman, Y. Roshan-Ali, *Journal of Chemical Technology and Biotechnology* 32, 920 (1982).
11. H. H. Szmant, D. D. Chundury, *Journal of Chemical Technology and Biotechnology* 31, 135 (1981).
12. K. Seri, Y. Inoue, H. Ishida, *Bulletin of the Chemical Society of Japan* 74, 1145 (2001).
13. H. E. van Dam, A. P. G. Kieboom, H. van Bekkum, *Starch* 38, 95 (1986).
14. K. M. Rapp, U.S. Pat. No. 4,740,605, issued Apr. 26, 1988.
15. F. Benvenuti et al., *Applied Catalysis A: General* 193, 147 (2000).
16. C. Carlini et al., *Applied Catalysis A: General* 183, 295 (1999).
17. U.S. Pat. No. 2,750,394, to Q. P. Peniston, issued Jun. 12, 1956.
18. T. El Hajj, A. MasRoua, J. C. Martin, G. Descotes, *Bulletin de la Societe Chimique de France* 5, 855 (1987).
19. L. Rigal, A. Gaset, J.-P. Gorrichon, *Industrial Engineering and Chemical Product Research Development* 20, 719 (1981).
20. C. Moreau et al., *Applied Catalysis A: General* 145, 211 (1996).
21. P. Rivalier, J. Duhamet, C. Moreau, R. Durand, *Catalysis Today* 24, 165 (1995).
22. The HMF yield and HMF concentration (in units of g/ml) as reported by different authors in representative systems are presented as follows: Dehydration system: HMF yield, HMF concentration, (reference numbers). DMSO: >95%, <0.13, (9-12). Polyethylene glycol/water: 60%, 0.28, (6, 13). Water, 34%, <0.06, (14). Water and water/miscible solvents: >75%, <0.04, (1, 10, 15,16). Biphasic systems: >75%, <0.02, (6, 17-20).
23. M. J. J. Antal, W. S. L. Mok, G. N. Richards, *Carbohydrate Research* 199, 91 (1990).
24. Y. Roman-Leshkov, J. N. Chheda, J. A. Dumesic, *Science* In Press.
25. A. S. Dias, M. Pillinger, A. A. Valente, *Journal of Catalysis* 229, 414 (2005).
26. C. Carlini, P. Patrono, A. M. R. Galletti, G. Sbrana, *Applied Catalysis A: General* 275, 111 (2004).
27. J. F. Harris, J. F. Saeman, L. L. Zoch, *Forest Products Journal* 10, 125 (1960).
28. R. H. Hunter, U.S. Pat. No. 3,201,331, issued Aug. 17, 1965.
29. R. E. Jones, H. B. Lange, U.S. Pat. No. 2,994,645, issued Aug. 1, 1961.
30. Published European Patent Application EP 0 082 689, to Barlow, M. T., Smith, D. J. & Steward, D. G., titled "Fuel composition," (1983).

What is claimed is:

1. A process to make furan derivative compounds, the process comprising:
   dehydrating a feedstock solution comprising a carbohydrate, in the presence of an acid catalyst, in a reaction vessel containing a biphasic reaction medium comprising an aqueous reaction solution and a substantially immiscible organic extraction solution;
   wherein the aqueous reaction solution, the organic extraction solution, or both the aqueous reaction solution and the organic extraction solution contain at least one modifier to improve selectivity of the process to yield furan derivative compounds, wherein the modifier is selected from the group of consisting of dimethylsulfoxide (DMSO), dimethylformamide, N-methylpyrrolidinone (NMP), acetonitrile, butyrolactone, dioxane, pyrrolidinone, and poly(1-vinyl-2-pyrrolidinone); and
   wherein the carbohydrate is dehydrated in the aqueous reaction solution to yield a furan derivative, and the furan derivative is extracted into the organic extraction solution.

2. The process of claim 1, wherein the aqueous reaction solution contains the acid catalyst and the aqueous reaction solution contains the modifier.

3. The process of claim 1, wherein the acid catalyst is selected from the group consisting of inorganic acids.

4. The process of claim 1, wherein the acid catalyst is a mineral acid.

5. The process of claim 1, wherein the acid catalyst is a zeolite.

6. The process of claim 1, wherein the acid catalyst is selected from the group consisting of silica-, silica-alumina-, and titania-based supports functionalized by acid groups.

7. The process of claim 1, wherein the acid catalyst is a cation exchange resin.

8. The process of claim 1, wherein the acid catalyst is a Lewis acid.

9. The process of claim 1, wherein the acid catalyst is selected from the group consisting of heteropolyacids, HCl, $HNO_3$, $H_2SO_4$, $H_3PO_4$, $H_3BO_3$, oxalic acid, levulinic acid, citric acid, $NbOPO_4$, and vanadium phosphate.

10. The process of claim 1, wherein the organic extraction solution comprises a solvent selected from the group consisting of water-immiscible, linear, branched, or cyclic alcohols, ethers, and ketones.

11. The process of claim 1, wherein the organic extraction solution comprises a solvent selected from the group consisting of unsubstituted aliphatic and aromatic hydrocarbons and halo-substituted aliphatic and aromatic hydrocarbons.

12. The process of claim 1, wherein the aqueous reaction solution further comprises at least one salt, thereby yielding a saline aqueous reaction solution.

13. The process of claim 12, wherein the at least one salt comprises a cation and an anion selected from the group consisting of acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, and bis-trifluorsulfonimide.

14. The process of claim 12, wherein the aqueous reaction solution comprises at least two different salts.

15. The process of claim 12, wherein the organic extraction solution comprises a solvent that is substantially immiscible in the saline aqueous reaction solution.

16. The process of claim 1, wherein aqueous reaction solution and the substantially immiscible organic extraction solution together yield an extraction ratio, R, of about 0.1 or greater.

17. The process of claim 1, wherein the organic extraction solution comprises a ketone selected from the group consisting of acetone, butanone, pentanone, hexanone, heptanone, diisobutylketone, 3-methyl-2-butanone, 5-methyl-3-heptanone, cyclobutanone, cyclopentanone, and cyclohexanone.

18. The process of claim 1, wherein the organic extraction solution and the aqueous reaction solution are present in a volume ratio of from about 0.1:1 to about 100:1 (organic extraction solution:aqueous reaction solution).

19. The process of claim 1, wherein the dehydration is carried out at a temperature ranging from about 70° C. to about 250° C.

20. The process of claim 1, comprising dehydrating the feedstock solution at a pressure ranging from about 1 bar to about 150 bars.

21. The process of claim 1, wherein the carbohydrate feedstock solution comprises 1-70 wt % carbohydrate.

22. The process of claim 1, wherein the organic extraction solution contains the modifier and the modifier is selected from the group consisting of a primary, secondary, linear, branched, or cyclic $C_1$- to $C_{12}$-alcohols.

23. The process of claim 22, wherein the modifier is selected from the group consisting of primary, secondary, linear, branched, or cyclic $C_1$- to $C_8$-alcohols.

24. The process of claim 22, wherein the organic phase modifier is 2-butanol.

25. A method of making a compound of Formula I:

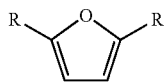

wherein each R is independently selected from the group consisting of hydrogen, $C_1$—$C_6$-alkyl, hydroxy-$C_1$—$C_6$-alkyl, acyl-$C_1$—$C_6$-alkyl, $C_1$—$C_6$-alkylcarbonyl-$C_1$—$C_6$-alkyl, and carboxy-$C_1$—$C_6$-alkyl, and provided the both R's are not simultaneously hydrogen, comprising:

dehydrating a feedstock solution comprising a carbohydrate, in the presence of an acid catalyst, in a reaction vessel containing a biphasic reaction medium comprising:

(i) an aqueous reaction solution comprising water, a salt, and a modifier selected from the group of consisting of dimethylsulfoxide (DMSO), dimethylformamide, N-methylpyrrolidinone (NMP), acetonitrile, butyrolactone, dioxane, pyrrolidinone and poly(1-vinyl-2-pyrrolidinone); and (ii) a substantially immiscible organic extraction solution; and wherein the carbohydrate is dehydrated in the aqueous reaction solution to yield a furan derivative, and the furan derivative is extracted into the organic extraction solution.

26. The method of claim 25, wherein the acid catalyst is selected from the group consisting of heteropolyacids, HCl, $HNO_3$, $H_2SO_4$, $H_3PO_4$, $H_3BO_3$, oxalic acid, levulinic acid, citric acid, $NbOPO_4$, and vanadium phosphate.

27. The method of claim 25, wherein the modifier comprises DMSO; and the immiscible organic extraction solution comprises a solvent selected from the group consisting of 1-butanol, DCM, MIBK, 2-butanol, and mixtures thereof.

* * * * *